(12) United States Patent
Huang et al.

(10) Patent No.: US 10,768,176 B2
(45) Date of Patent: Sep. 8, 2020

(54) HETERO FUNCTIONAL BINDING SYSTEMS

(71) Applicant: Anteo Technologies Pty Ltd, Eight Mile Plains (AU)

(72) Inventors: Chang-yi Huang, Calamvale (AU); Nobuyoshi Joe Maeji, Wishart (AU)

(73) Assignee: ANTEO TECHNOLOGIES PTY LTD, Eight Mile Plains (AU)

( * ) Notice: Subject to any disclaimer, the term of this patent is extended or adjusted under 35 U.S.C. 154(b) by 334 days.

(21) Appl. No.: 15/319,269

(22) PCT Filed: Jun. 17, 2015

(86) PCT No.: PCT/AU2015/050335
§ 371 (c)(1),
(2) Date: Dec. 15, 2016

(87) PCT Pub. No.: WO2015/192183
PCT Pub. Date: Dec. 23, 2015

(65) Prior Publication Data
US 2017/0115285 A1      Apr. 27, 2017

(30) Foreign Application Priority Data

Jun. 17, 2014  (AU) .............................. 2014902315

(51) Int. Cl.
*G01N 33/553*      (2006.01)
*C07F 11/00*       (2006.01)
*G01N 33/531*      (2006.01)
*G01N 33/543*      (2006.01)

(52) U.S. Cl.
CPC .......... *G01N 33/553* (2013.01); *C07F 11/005* (2013.01); *G01N 33/531* (2013.01); *G01N 33/54313* (2013.01)

(58) Field of Classification Search
None
See application file for complete search history.

(56) References Cited

U.S. PATENT DOCUMENTS

| 4,637,839 A | 1/1987 | Hall |
| 9,234,891 B2* | 1/2016 | Muir ..................... C07K 17/06 |

| 2003/0027354 A1* | 2/2003 | Geli ................. G01N 27/44704 436/178 |
| 2004/0063220 A1* | 4/2004 | Lebrun ................ B01J 19/0046 506/18 |
| 2010/0311080 A1* | 12/2010 | Cao ........................ C01B 19/007 435/7.1 |
| 2013/0066077 A1* | 3/2013 | Maeji ..................... C07K 17/14 546/2 |
| 2016/0178636 A1* | 6/2016 | Maeji ................... G01N 33/587 435/7.1 |
| 2018/0097233 A1* | 4/2018 | Huang ................. H01M 4/366 |

FOREIGN PATENT DOCUMENTS

| EP | 2062921 A1 | 5/2009 |
| GB | 748391 | 5/1956 |
| GB | 1124499 | * 8/1968 |
| WO | WO 84/03093 | 8/1984 |
| WO | WO 2006/002472 A1 | 1/2006 |
| WO | WO 2007/076580 A1 | 7/2007 |
| WO | WO 2009/097319 A2 | 8/2009 |
| WO | WO 2011/140590 A1 | 11/2011 |

OTHER PUBLICATIONS

Hauserman ("Chromium Complexes," Advances in Chemistry, vol. 23, chapter 32, pp. 338-356, published Jan. 1, 1959) (Year: 1959).*
International Search Report and Written Opinion, PCT/AU2015/050335, dated Aug. 17, 2015.
Muir BW et al. High-throughput optimization of surfaces for antibody immobilization using metal complexes. Analytical Biochemistry. 2007; 363: 97-107.
Ooi et al., Coordination complexes as molecular glue for immobilization of antibodies on cyclic olefin copolymer surfaces, Analytical Biochemistry, vol. 456, 2014, pp. 6-13, Abstract only.
Extended European Search Report corresponding to EP 15810549.4; dated Jan. 8, 2018 (9 pages).

* cited by examiner

*Primary Examiner* — Tracy Vivlemore
*Assistant Examiner* — Nam P Nguyen
(74) *Attorney, Agent, or Firm* — Myers Bigel, P.A.

(57) ABSTRACT

The present invention relates to reagents and methods for binding compounds to surfaces that are hydrophobic. More specifically, the invention relates to simple methods for coating of hydrophobic planar, membrane or particle surfaces to facilitate binding of molecules such as labels, dyes, synthetic and biological polymers and/or nanoparticles thereto.

12 Claims, 9 Drawing Sheets

A.

B.

C.

A.

B.

C.

HETERO FUNCTIONAL BINDING SYSTEMS

RELATED APPLICATIONS

This application is a 35 U.S.C. § 371 national phase entry of PCT Application PCT/AU2015/050335, filed Jun. 17, 2015, and published in English on Dec. 23, 2015, as International Publication No. WO 2015/192183, and which claims the benefit of Australian Application No. 2014902315, filed Jun. 17, 2014, the disclosure of each of which is incorporated herein by reference in its entirety.

FIELD OF THE INVENTION

The present invention relates to reagents and methods for binding compounds to surfaces that are (at least partially) hydrophobic. More specifically, the invention relates to simple methods for coating of hydrophobic planar, membrane or particle surfaces to facilitate binding of molecules such as labels, dyes, synthetic and biological polymers and/or nanoparticles thereto.

BACKGROUND OF THE INVENTION

There is a need for simple coating methods to bind molecules on all types of materials whose pre-existing surface is not suitable for such applications. Molecules (such as peptides, proteins, polynucleotides, polycarbohydrates, drugs, dyes, labels, synthetic polymers and particles) attached to surfaces are used in many applications in life sciences research (such as drug discovery, diagnostics, imaging and drug delivery), as well as non-life science applications (such as electronics and catalysis), There are currently many approaches to forming such systems (e.g. those described in Hermanson, et al., *Bioconjugate Techniques*: Academic Press, 1996. and Sperling, R. A., Parak, W. J., "Surface modification, functionalization and bioconjugation of colloidal inorganic nanoparticles", *Phil. Trans. R. Soc A* 368; 1333-1383, 2010).

The metal complexes described in WO 2006/002472 and WO 2011/140590 can be used to bind a variety of molecules to surfaces that have electron-donating species. Where the surfaces of the substrates used are hydrophobic (e.g. quantum dots, certain polymers, plastics and metals), they generally do not have electron-donating species (which tend to be associated with hydrophilic surfaces) and therefore need to be modified or treated in some way to generate more hydrophilic functionalities in order to actively bind molecules such as proteins, polynucleotides, etc. Without such treatments, passive binding to such hydrophobic surfaces commonly leads to denaturing and loss of functionality of many biological molecules, such as proteins.

However, existing treatment methods such as sputter coating, gamma or electron-beam irradiation, or plasma treatment are hard to control, require specialised equipment and do not have the potential of creating a diversity of different coatings. In addition, such techniques produce regions of differing hydrophobicities resulting in poor surface uniformity. Methods to form functional groups to covalently couple molecules on hydrophobic surfaces also have similar problems of poor surface uniformity.

It would be advantageous to have a method for attaching molecules to hydrophobic surfaces that is not labour-intensive, that does not require specialised equipment and that allows substrates to be produced that allow molecules to be attached in a uniform and/or controllable arrangement.

Reference to any prior art in the specification is not, and should not be taken as, an acknowledgment or any form of suggestion that this prior art forms part of the common general knowledge in any jurisdiction or that this prior art could reasonably be expected to be understood and regarded as relevant by a person skilled in the art.

SUMMARY OF THE INVENTION

The present inventors have found that modified metal complexes can be used to form hetero bi-functional binding systems that allow various molecules to be attached or bound to hydrophobic surfaces.

In one aspect, the present invention relates to a modified substrate for binding of a target molecule thereon, the substrate including:
 a surface that is hydrophobic, and
 a metal complex including a metal ion, the metal ion having:
  (i) one or more co-ordination sites occupied by a hydrophobic ligand for binding the metal complex to the hydrophobic surface, and
  (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface.

The modified substrate may include a target molecule bound thereto.

In another aspect, the present invention relates to a method of modifying a hydrophobic surface, the method including:
 providing a surface that is hydrophobic,
 contacting the surface with a metal complex, the metal complex including a metal ion having:
  (i) one or more co-ordination sites occupied by a hydrophobic ligand for binding the metal complex to the hydrophobic surface, and
  (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface,
thereby forming a surface having increased hydrophilicity.

The method may include the further step of contacting the treated surface with a target molecule thereby binding the target molecule to the surface.

In another aspect, the present invention relates to a method for binding a target molecule to a substrate, the method including:
 providing a substrate including a surface that is hydrophobic,
 contacting the surface with a metal complex, the metal complex including a metal ion having:
  (i) one or more co-ordination sites occupied by a hydrophobic ligand for binding the metal complex to the hydrophobic surface, and
  (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface, contacting a target molecule with the metal complex, thereby binding the target molecule to the substrate.

In another aspect, the present invention relates to a metal complex for use, or when used, in the methods of the present invention.

In another aspect, the present invention relates to a composition including a metal complex for use, or when used, in the methods of the present invention.

In another aspect, the present invention relates to a composition including a metal complex, the metal complex including a metal ion, the metal ion having:
  (i) one or more co-ordination sites occupied by a hydrophobic ligand for binding the metal complex to a hydrophobic surface, and
  (ii) one or more co-ordination sites available for binding to a target molecule.

In one embodiment, the composition is for use, or when used, in the methods of the present invention.

In another aspect, the present invention relates to a particle, the particle including:
  a surface that is hydrophobic, and
  a metal complex including a metal ion, the metal ion having:
    (i) one or more co-ordination sites occupied by a hydrophobic ligand for binding the metal complex to the hydrophobic surface, and
    (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface.

The particle may be completely coated with the metal complex.

The particle may further include a target molecule bound to the particle.

In another aspect, the present invention also relates to a coating for a substrate, the coating including a metal complex, the metal complex including a metal ion, the metal ion having:
  (i) one or more co-ordination sites occupied by a hydrophobic ligand for binding the metal complex to a hydrophobic surface, and
  (ii) one or more co-ordination sites available for binding to a target molecule.

The metal complex may form an oligomer with other metal complexes in the coating. The metal complex can be oligomerised prior to coating the substrate, or oligomerised during or after coating the substrate.

DETAILED DESCRIPTION OF THE EMBODIMENTS

Figure 1:
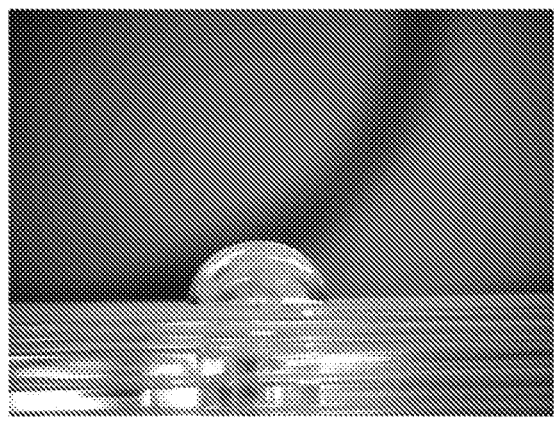
FIG. 1. A. Contact angle of untreated PS surfaces, B. Contact angle of treated (1) PS surface (treated with the metal-hydrophobic ligand complex of Example 5A), C. Contact angle of treated (2) PS surface (treated with the metal-hydrophobic ligand complex of Example 2A).
Figure 1:
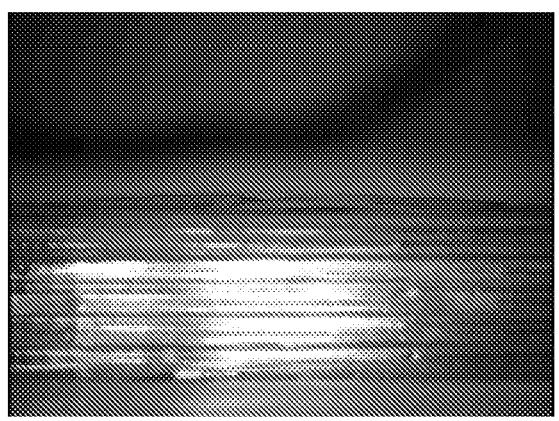
Figure 1:
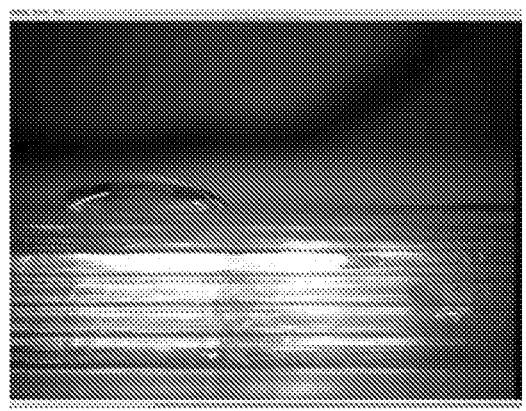

The present invention provides a way of forming binding surfaces using substituted metal complexes with two distinct binding faces that are able to form coatings and bind target molecules to substrates.

Metal complexes linking biomolecules to various surfaces are described in WO 2006/002472 and WO 2011/140590. In particular, metal complexes as described in these publications allow strong but gentle binding interactions to be formed that minimise damage to biomolecules (such as proteins) on many different surfaces.

However, binding of metal complexes to surfaces would be expected to be determined by coordination forces which implies that the surface has electron-donating species. While the prior art referred to above is not restricted to a particular type of surface/material, it would be expected that its performance would be most effective on surfaces having predominantly hydrophilic regions (i.e. regions possessing electron-donating groups). This is evidenced by the fact that polypropylene (PP) tubes, which have hydrophobic surfaces (i.e. surfaces having little or no electron-donating groups), are used in the examples, and that such materials do not bind metal complexes.

The binding strength of the complexes in this prior art is affected by the absence or poor distribution of functionalities that can potentially bind to metal complexes. Such situations are most common in predominantly hydrophobic surfaces. For example, there are injection-moulded polymers such as polystyrene (PS), cyclic olefin copolymers (COC/COP), polycarbonates (PC) and other thermoplastics that are often very hydrophobic, and, as discussed above, require some form of surface treatment to generate more hydrophilic functionalities and thereby allow binding of proteins, nucleotides, etc to the surface. Where the surface is hydrophilic, the choices for binding depend on whether there are functional groups for covalent coupling or charge attraction is used for coatings. Each material has commonly-used surface modification and/or coating methods in order to bind biological as well as synthetic molecules. There are currently no simple methods to form coatings across a range of highly hydrophobic to highly hydrophilic materials and form a binding surface as described above.

Where the substrate to be modified is a particle, it is important to realise that as particles become smaller and smaller (down to micro-, and in particular, nano-metre dimensions), any coatings used to bind other molecules to the particles should also become proportionally thinner. For example, the colour of colloid gold is determined by its shape and size, its optical properties originate from localised surface plasmon resonance, and as a consequence of shape anisotropy, a sphere-shaped particle is distinctly different to a rod-shaped particle in its optical and hydrodynamic properties (Sharma V., Park, K., Srinivasarao, M. (2009) "Colloidal dispersion of gold nanorods", *Materials Science and Engineering;* 1-38). Therefore, there is a need to maintain the bulk properties of the underlying material, limit exposure of the external environment to the underlying material, and/or protect the underlying material from the external environment.

Examples of this are magnetic nanoparticles used as MRI contrast agents, and other particles used in in vivo applications that may require protection from the biological environment. Oxidation can easily affect, in a detrimental way, the magnetic properties of a magnetic nanoparticle (Harris, L. A., Goff, J. D. et al. (2003) "Magnetite nanoparticle dispersions stabilized with triblock copolymers", *Chemical Materials*). To minimise such problems, as well as maintain the colloidal stability and dispersibility of particles in biological environments, the actual magnetite content of magnetic nanoparticles can be decreased, as can other inherent properties of the nanoparticle (such as the optical absorption, photoluminescense, phosphorescence of the nanoparticles, assuming some constant size).

An example where one may wish to limit the exposure of the external environment to the underlying material occurs with particles having some potential cytotoxicity (such as semi-conductor quantum dots). Quantum dots (QDots) are made with elements that are inherently toxic to cells and living systems.

Therefore, there is a need to be able to coat the underlying material, activate it for binding molecules or for further improved protection, as well as to make surfaces water-compatible so that colloidal stability is maintained and no aggregation/clumping occurs.

There are three basic approaches to forming a coating on gold colloids: charge attraction of the negative gold particles to positively charged polymers, hydrophobic absorption, and dative binding to thiols. Charge attraction is pH-dependent and reversible (i.e., not stable) and hydrophobic interactions are hard to control (and in the worst case, lead to fouling and most likely aggregation/clumping of the particles). Finally, binding to a thiol is usually done to produce some functional group for subsequent covalent coupling. Depending on the subsequent steps, the critical issue of controlling coatings and binding other molecules without destroying colloidal stability remains a difficult issue.

The present inventors have found that by using modified metal complexes it is possible to form strong binding surfaces from surfaces not otherwise suited to metal chelation (in particular, hydrophobic surfaces) and in situations of poor surface uniformity (i.e. where the surface includes regions of different hydrophobicities). In addition, the modified metal complexes can form thin coats on surfaces (in particular, particles) that have the desired dimensions and that can maintain the bulk properties of the underlying material, limit exposure of the external environment to the underlying material, and/or protect the underlying material from the external environment.

In one aspect, the present invention relates to a modified substrate for binding of a target molecule thereon, the substrate including:
   a surface that is hydrophobic, and
   a metal complex including a metal ion, the metal ion having:
      (i) one or more co-ordination sites occupied by a hydrophobic ligand for binding the metal complex to the hydrophobic surface, and
      (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface.

With regard to the substrate, any solid substrate that includes a surface or regions of a surface (whether two dimensional or within a three dimensional matrix) and that requires coating and binding of target molecules thereon can be used in the present invention. In particular, any substrate that has hydrophobic character on some or all of its surface regions can be used in the present invention. The substrate will be composed of any suitable material, and suitable substrates for use in the present invention include those composed of metals (such as gold, silver, platinum, iridium, titanium and aluminium), metal or metalloid composites (comprising the metals mentioned above, as well as steel, ceramics, silica and those used to produce materials such as QDots), synthetic polymers (polystyrene, cyclic olefin copolymers, polycarbonates, polyvinyl ethers, polyacrylamides, polymethacrylates, polyvinylidene fluorides and polyvinyl-alcohols), biological materials (e.g. biopolymers, including substituted polysaccharides such as nitrocellulose, cellulose acetate, etc), glass, ceramic, metal oxides (such as iron oxide, titanium oxide and silver oxide) and carbon.

Some substrates, depending on their history and manufacture, may be potentially hydrophilic or hydrophobic despite the characteristics of the bulk material. Examples of hydrophobic materials having potentially hydrophilic character on their surfaces may include injection-moulded polystyrene which may result in oxidation or other modification under certain moulding conditions. Examples of hydrophilic materials having potentially hydrophobic character on their surfaces may include silica oxide, which, due to different hydrogen-bonding patterns or passive binding of contaminants from the atmosphere, results in a substantially hydrophobic surface.

The substrate may be substantially flat or planar, or micro-patterned (via injection moulding). The substrate can also be a woven, porous or matted material, a gel or a polymer network. Examples of such substrates include microarray slides, microtitre plates, lateral flow materials, and binding/non-binding surfaces used in biosensors and similar devices.

The substrate may have more of a spherical shape (e.g. is a particle). As used herein, the term "particle" refers to a small object that behaves as a whole unit with respect to its transport and properties i.e. a discrete unit of matter, where the atoms or molecules from which it is formed essentially embody the particle. Generally, the particle used in accordance with the present invention will be a microparticle. A smaller particle (such as a nanoparticle) can also be used. Where the particle is a microparticle, typical sizes suitable for use in the present invention include microparticles of less than about 10 micrometers (for example, about 5 micrometers or less, or about 3 micrometers or less). By "nanoparticle" it is intended to mean particles having a diameter below about 1000 nm (for example, about 500 nm) and more specifically below about 300 nm. Preferably, the diameter of the nanoparticle is less than about 250 nm (for example, less than about 220 nm). A diameter range of between about 5 and about 200 nm is suitable. In one embodiment, the term "nanoparticle" refers to particles having diameters in the nano size range, which do not cross over into the micron size range.

Any hydrophobic nanoparticle or microparticle known in the art can be used in the present invention. Examples of nanoparticles and microparticles suitable for the particle of the invention include those composed of the materials discussed above.

Magnetic particles, which are composed of one or more of the species mentioned above, are also intended to be within the scope of the term "particle". Therefore, the particles may be formed from a heterogeneous mixture of substrate molecules or a heterogeneous mixture of atoms, or may be formed from one type of atom. In one embodiment, the particle defines a substantially spherical form.

The particle does not require to be fully dispersed in aqueous solution to be used in the invention. As substituted metal complexes are also soluble in organic solvents, completely hydrophobic particles such as Quantum Dots that require organic solvents can be coated and transferred into the aqueous phase by the use of substituted metal complexes. Such surfaces are charged, helping to maintain colloidal stability in aqueous solution. Additionally, these metal complexes can undergo further modifications, as required. If the hydrophobic layer of the metal complex is insufficient as a protective coating, addition of other target molecules (e.g. polymers such as polyvinylalcohol, polyacetic acids, etc) to bind and cross-link the metal complex on the substrate can be achieved. Such doubly-coated substrates can be subsequently used to bind target molecules such as proteins. In this way, metal complexes can be used to coat hydrophobic particles that are not normally miscible in aqueous solutions, without clumping.

With regard to the substrate surface, the term "hydrophobic" means that the surface of the substrate includes one or more regions of hydrophobicity. The surface may be completely hydrophobic (i.e. completely composed of hydrophobic regions). Alternatively, the surface may be composed of a mixture of hydrophilic and hydrophobic regions.

Hydrophobic molecules or compounds are "water-fearing" (i.e. do not dissolve in water), tend to be non-polar and, therefore, prefer other neutral molecules and non-polar solvents to polar solvents and charged or polar molecules (such as water, short-chain alcohols, and the like). Water on hydrophobic surfaces will exhibit a high contact angle.

The surface may have non-uniform distribution. For example, the surface may have a greater percentage of hydrophilic regions than hydrophobic regions, which hydrophilic regions are dispersed amongst the hydrophobic regions. Such an example may include gamma or plasma-irradiated PS surfaces or where co-polymerisation of polar and non-polar monomers in the synthesis of particles leads to non-uniform surfaces. The use of metal complexes in accordance with the invention on such surfaces is discussed further below.

As used herein, the term "target molecule" refers to any molecule that it is desired to be bound to or immobilised on the substrate. The target molecule may be selected from proteins, polynucleotides, carbohydrates, lipids, drugs, small molecules, labelling agents, synthetic polymers and nanoparticles. The protein may be an antibody, streptavidin, Protein A, Protein G, a lipoprotein or a glycoprotein. Examples of polynucleotides include DNA and RNA. Suitable carbohydrates include polysaccharides (whether substituted or unsubstituted). Synthetic polymers (such as polyvinyl alcohols, dextrans, polyacrylic acids and poly (hydroxymethacrylates)) or nanoparticles that allow the formation of multi-layer coatings may also be used in the present invention to maintain the bulk properties of the underlying material, limit exposure of the external environment to the underlying material, and/or protect the underlying material from the external environment. The coatings formed are stable to storage but in the presence of target molecules (such as proteins) can bind target molecules.

The target molecule can be any molecule with electron donating potential to form stable coordination bonds to the metal ion of the metal complex. The target molecule may be bound directly to the metal ion (i.e. it is not modified prior to use in the method of the present invention). The target molecule or the ion may include a linker that binds the target molecule to the metal ion via the linker.

The modified substrate may include a target molecule bound thereto.

As stated above, the metal complex according to the invention includes a metal ion having one or more co-ordination sites occupied by a hydrophobic ligand.

The metal ion may be a transition metal ion. As used herein, the term "transition metal ion" refers to an element whose atom has an incomplete d sub-shell, or which can give rise to cations with an incomplete d sub-shell. Metal ions that may be used are selected from the group consisting of aluminium, rhodium, scandium, titanium, vanadium, chromium, ruthenium, platinum, manganese, iron, cobalt, nickel, copper, molybdenum, zirconium, and zinc ions. Chromium, ruthenium, iron, cobalt, aluminium, zirconium and rhodium are preferred. Particularly preferred are chromium and further, where the chromium has an oxidation state of Ill. Other oxidation states of chromium include I, II, IV, V and VI. Where the coating layer includes chromium, the coating layer may further include transition metal ions other than chromium. In addition, mixtures of different metal ions may be used (for example, the surface may be coated with two or more, three or more, or four or more different metal complexes that include different metal ions).

With regard to "hydrophobic ligand", in principle, any species that includes a hydrophobic group and an electron-donating group (for binding to the metal ion) can act as a hydrophobic ligand.

In general terms, the metal complexes of the present invention take the form (R—X)-M, where:
  R is a group selected and optimised to preferentially bind various substrates (in particular, hydrophobic substrates) by hydrophobic interaction,
  X is a chelating group able to coordinate the R group on some (but not all) of the available coordination sites of a metal ion, and
  M is a transition metal ion (or oligomers of transition metal ions) having at least one "free" coordination sites that is available for binding to a target molecule.

Through R—X, the metal complex is able to interact with, or bind to, the hydrophobic surface by non-covalent hydrophobic interactions, thereby forming a region, film or coating of metal ions on the surface of a substrate.

The hydrophobic ligand (R—X) in this invention coordinates to a metal ion via X, where X may be any electron-donating group that is able to form a co-ordination bond with the metal ion. Examples include groups having an acid or amine-containing group forming a co-ordination bond with the metal ion. Groups such as carboxylic acid, aldehyde, and polyalcohol are particularly useful but generally any chelating groups that are able to bind to metal ions with sufficient stability to form the substituted metal complex can be used in the present invention. It is reasonable to expect that a bi-dentate carboxylic acid functional group contributes coordinate bonds with respect to its carbonyl oxygen and hydroxyl oxygen of the carboxyl group with one or more metal ions. Analogous acid functionality in polydentate sulfonic, phosphonic, phosphate and bisulfite acids, and, including similar polydentate acidic structures would comparably associate with trivalent metal ions such as chromium to some or an equivalent degree.

"R" may be independently selected from alkyl, heteroalkyl, alkenyl, alkynyl, cycloalkyl, heterocycloalkyl, alkylcycloalkyl, heteroalkylcycloalkyl, aryl, heteroaryl, aralkyl and heteroaralkyl, which groups are optionally substituted, The term "alkyl" refers to a saturated, straight-chain or branched hydrocarbon group that contains from 1 to 20 carbon atoms, preferably from 1 to 12 i.e. 1, 2, 3, 4, 5, 6, 7, 8, 9, 10, 11 or 12 carbon atoms, for example a n-octyl group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl.

The term "heteroalkyl" refers to an alkyl group as defined above that contains one or more heteroatoms selected from oxygen, nitrogen and sulphur (especially oxygen and nitrogen). Specific examples of heteroalkyl groups are methoxy, trifluoromethoxy, ethoxy, n-propyloxy, iso-propyloxy, butoxy, tert-butyloxy, methoxymethyl, ethoxymethyl, —$CH_2CH_2OH$, —$CH_2OH$, methoxyethyl, 1-methoxyethyl, 1-ethoxyethyl, 2-methoxyethyl or 2-ethoxyethyl, methylamino, ethylamino, propylamino, iso-propylamino, dimethylamino, diethylamino, iso-propyl-ethylamino, methylamino methyl, ethylamino methyl, di-iso-propylamino ethyl, methylthio, ethylthio, iso-propylthio, enol ether, dimethylamino methyl, dimethylamino ethyl, acetyl, propionyl, butyryloxy, acetyloxy, methoxycarbonyl, ethoxy-carbonyl, propionyloxy, acetylamino, propionylamino, carboxymethyl, carboxyethyl or carboxypropyl, N-ethyl-N-methylcarbamoyl and N-methylcarbamoyl. Further examples of heteroalkyl groups are nitrile, iso-nitrile, cyanate, thiocyanate, iso-cyanate, iso-thiocyanate and alkylnitrile groups.

The term "alkenyl" refers to an at least partially unsaturated, straight-chain or branched hydrocarbon group that contains from 2 to 20 carbon atoms, preferably from 2 to 10 carbon atoms, especially from 2 to 6, i.e. 2, 3, 4, 5 or 6, carbon atoms. Specific examples of alkenyl groups are ethenyl (vinyl), propenyl (allyl), iso-propenyl, butenyl, ethinyl, propinyl, butinyl, iso-prenyl and hex-2-enyl group. Preferably, alkenyl groups have one or two double bond(s).

The term "alkynyl" refers to a at least partially unsaturated, straight-chain or branched hydrocarbon group that contains from 2 to 20 carbon atoms, preferably from 2 to 10 carbon atoms, especially from 2 to 6, i.e. 2, 3, 4, 5 or 6, carbon atoms. Specific examples of alkynyl groups are ethynyl, propynyl, butynyl, acetylenyl and propargyl groups. Preferably, alkynyl groups have one or two (especially preferably one) triple bond(s).

The term "cycloalkyl" refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. Specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0] nonyl, tetraline, adamantane (i.e. tricycle[3.3.1.13,7]decane), cyclopentylcyclohexyl and cyclohex-2-enyl.

The term "heterocycloalkyl" refers to a cycloalkyl group as defined above in which one or more (preferably 1, 2 or 3) ring carbon atoms, each independently, have been replaced by an oxygen, nitrogen, silicon, selenium, phosphorus or sulfur atom (preferably by an oxygen, sulfur or nitrogen atom). A heterocycloalkyl group has preferably 1 or 2 rings containing from 3 to 10 (especially 3, 4, 5, 6 or 7) ring atoms (preferably selected from C, O, N and S). Specific examples are piperidyl, prolinyl, imidazolidinyl, piperazinyl, morpholinyl, urotropinyl, pyrrolidinyl, tetra-hydrothiophenyl, tetrahydropyranyl, tetrahydrofuryl and 2-pyrazolinyl group and also lactames, lactones, cyclic imides and cyclic anhydrides.

The term "alkylcycloalkyl" refers to a group that contains both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two ring systems having from 3 to 10 (especially 3, 4, 5, 6 or 7) ring carbon atoms, and one alkyl, alkenyl or alkynyl group having 1 or 2 to 6 carbon atoms. Preferably, the alkyl, alkenyl or alkynyl groups form a bi- or tri-cyclic ring system with the cycloalkyl group and/or are the means by which the cycloalkyl group is joined to the compound of formula (I) or (II).

The term "heteroalkylcycloalkyl" refers to alkylcycloalkyl groups as defined above in which one or more, preferably 1, 2 or 3, carbon atoms have been replaced independently of each other by an oxygen, nitrogen, silicon, selenium, phosphorus or sulfur atom (preferably by an oxygen, sulfur or nitrogen atom). A heteroalkylcycloalkyl group preferably contains 1 or 2 ring systems having from 3 to 10 (especially 3, 4, 5, 6 or 7) ring atoms, and one or two alkyl, alkenyl, alkynyl or heteroalkyl groups having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkyl-heterocycloalkyl and heteroalkylheterocycloalkenyl, the cyclic groups being saturated or mono-, di- or tri-unsaturated.

The term "aryl" refers to an aromatic group that contains one or more rings containing from 6 to 14 ring carbon atoms, preferably from 6 to 10 (especially 6) ring carbon atoms. Examples are phenyl, naphthyl and biphenyl groups.

The term "heteroaryl" refers to an aromatic group that contains one or more rings containing from 5 to 14 ring atoms, preferably from 5 to 10 (especially 5 or 6) ring atoms, and contains one or more (preferably 1, 2, 3 or 4) oxygen, nitrogen, phosphorus or sulfur ring atoms (preferably 0, S or N). Examples are pyridyl (for example, 4-pyridyl), imidazolyl (for example, 2-imidazolyl), phenylpyrrolyl (for example, 3-phenylpyrrolyl), thiazolyl, iso-thiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (for example, 3-pyrazolyl) and iso-quinolinyl groups.

The term "aralkyl" refers to a group containing both aryl and also alkyl, alkenyl, alkynyl and/or cycloalkyl groups in accordance with the above definitions, such as, for example, an arylalkyl, arylalkenyl, arylalkynyl, arylcycloalkyl, arylcycloalkenyl, alkylarylcycloalkyl and alkylarylcycloalkenyl group. Preferably, the alkyl, alkenyl or alkynyl groups provide the means by which the alkyl group is joined to the compound of formula (I) or (II). Specific examples of aralkyls are 1H-indene, tetraline, dihydronaphthalene, indanone, phenylcyclopentyl, cyclohexylphenyl, fluorene and indane. An aralkyl group preferably contains one or two aromatic ring systems (1 or 2 rings) containing from 6 to 10 carbon atoms and one alkyl, alkenyl and/or alkynyl group containing from 1 or 2 to 6 carbon atoms and/or a cycloalkyl group containing 5 or 6 ring carbon atoms.

The term "heteroaralkyl" refers to an aralkyl group as defined above in which one or more (preferably 1, 2, 3 or 4) carbon atoms, each independently, have been replaced by an oxygen, nitrogen, silicon, selenium, phosphorus, boron or sulfur atom (preferably oxygen, sulfur or nitrogen). That is, a group containing aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one alkyl, alkenyl and/or alkynyl group containing 1 or 2 to 6 carbon atoms and/or a cycloalkyl group containing 5 or 6 ring carbon atoms, wherein 1, 2, 3 or 4 of these carbon atoms have been replaced by oxygen, sulfur or nitrogen atoms. Preferably, the alkyl, alkenyl or alkynyl group provides the means by which the alkyl group is joined to the compound of formula (I) or (II).

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, heteroarylheterocycloalkenyl, heteroarylalkyl-cycloalkyl, heteroarylalkylheterocycloalkenyl, heteroarylheteroalkylcycloalkyl, heteroarylheteroalkylcycloalkenyl and heteroarylheteroalkylheterocycloalkyl groups, the cyclic groups being saturated or mono-, di- or tri-unsaturated. Specific examples are tetrahydroisoquinolinyl and benzoyl.

The term "optionally substituted" refers to a group in which one, two, three or more hydrogen atoms have been replaced independently of each other by, for example, halogen (for example, fluorine, chlorine, bromine or iodine atoms) or by, for example, OH, $CH_3$, $CH_2CH_3$, $=O$, SH, $=S$, $NH_2$, NH alkyl, $=NH$, $N_3$ or $NO_2$ groups. This expression also refers to a group that is substituted by one, two, three or more (preferably unsubstituted) alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl groups.

As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

In accordance with the present invention, "R" is required to be a hydrophobic group. In the example where X is a carboxylic acid, R—X may be acetic, butyric, hexanoic, abietic, angelic, tiglic, crotonic, lauric, linoleic, linolenic, perfluorinated, gluconic, methacrylic, malonic, succinic, phthalic, acrylic, alpha- and beta-furyl acrylic acid, propiolic, myristic, palmitic, stearic, naphthoic, naphthenic, 6-aminohexanoic, benzoic, polyconjugated carboxylic acid (e.g. sorbic, isocrotonic, phenylacetic), cyclic carboxylic acid, 3-butenoic, 7-octenoic, 9-decenoic, 11-dodecenoic, oleic, 2-cyclopentene-1-acetic, cinnamic, behenic, biphenyl-4-carboxylic acid, and the like, as well as salts thereof. In one embodiment, the acid is selected from the following carboxylic acids: stearic, hexanoic, butyric (including sodium butyrate), lauric, benzoic, 1-naphthoic, malonic, sorbic and bi-phenyl-4 carboxylic acid, dimethylamine-boranecarboxylic acid, 2-bromo-2-methylpropionic acid, 2-(bromomethyl)acrylic acid, 4-bromobutyric acid, 3-chloro-2,2-dimethylpropionic acid, 5-chlorovaleric acid, 4,4,4-trifluorobutyric acid, 1-(trifluoromethyl)cyclopropane-1-carboxylic acid, 4,4-difluorocyclohexanecarboxylic acid, 2-fluorophenylacetic acid, 4-fluorophenoxyacetic acid, n-phenylglycine, 4-(3-pyrrolyl)butyric acid, (2-methylphenoxy)acetic acid, (4-methylphenoxy)acetic acid, phenoxyacetic acid, 3-phenoxypropionic acid, adipic acid monoethyl ester, 1-ethoxycarbonyl cyclobutane-1-carboxylic acid, benzyloxyacetic acid, 2-methoxyphenylacetic acid, 3-methoxyphenylacetic acid, 4-methoxyphenylacetic acid, 4-methoxycyclohexanecarboxylic acid, mixture of cis and trans 2-hexynoic acid, 2-pentynoic acid, 2-butynoic acid, 3-cyclopropyl-2-propynoic acid, 2-propylacrylic acid, 2-ethylacrylic acid, 4-methyl-2-oxovaleric acid, phenylglyoxylic acid, 2,2-dimethylvaleric acid, 2,2-dimethylbutyric acid, 2,2-dimethyl-4-pentenoic acid, pivalic acid, 2-ethylbutyric acid, 3,3-dimethylbutyric acid, isovaleric acid, 4-pentynoic acid, 4-methylvaleric acid, 5-hexynoic acid, 6-heptynoic acid, 7-oxooctanoic acid, heptanoic acid, 6-heptenoic acid, valeric acid, 5-hexenoic acid, 3-cyclopentylpropionic acid, phenylacetic acid, cyclopentylacetic acid, cyclohexaneacetic acid, 1-methyl-1-cyclohexanecarboxylic acid, 2,2,3,3-tetramethylcyclopropanecarboxylic acid, 4-methyl-1-cyclohexanecarboxylic acid, cyclobutanecarboxylic acid, cyclopentanecarboxylic acid, cyclohexanecarboxylic acid, cycloheptanecarboxylic acid, (trimethylsilyl)acetic acid, 3-(trimethylsilyl)propynoic acid, 5-bromovaleric acid, iodoacetic acid, 3-iodopropionic acid, 4-iodobutyric acid, 4-carboxy-tempo free radical, 2-formylphenoxyacetic acid, (2-methoxyphenoxy)acetic acid, 4-formylphenoxyacetic acid, suberic acid monomethyl ester, (2,5-dimethoxyphenyl)acetic acid, 3,4-dimethoxyphenylacetic acid, (2,4-dimethoxyphenyl)acetic acid, (3,5-dim ethoxyphenyl)acetic acid, 1,4-benzodioxane-6-acetic acid, 3,4-(methylenedioxy)phenylacetic acid, 3-(3,4-methylenedioxyphenyl)propionic acid, dibromoacetic acid, n-boc-1-aminocyclobutane carboxylic acid, boc-Inp-OH, 1-boc-4-piperidylacetic acid, 2,4,6-trimethoxyphenylacetic acid, 5-bromobenzo[1,3]dioxole-4-carboxylic acid, 4-bromo-3-methyl-1H-pyrazole-5-carboxylic acid, 4-bromopyrrole-2-carboxylic acid, 2-bromopyridine-3-carboxylic acid, 5-bromo-2-furoic acid, 2-bromofuran-3-carboxylic acid, 3-chloropyridine-2-carboxylic acid, 2-chloro-6-methoxypyridine-4-carboxylic acid, 6-chloropyridine-2-carboxylic acid, 6-chloropyridine-3-carboxylic acid, 2-chloropyridine-4-carboxylic acid, 2-chloropyridine-3-carboxylic acid, 6-methylpyridine-2-carboxylic acid hydrochloride hydrate, trigonelline hydrochloride, 2-fluoro-6-methoxybenzoic acid, 3-fluoro-4-methoxybenzoic acid, 2-fluorobenzoic acid, 3,5-difluoropyridine-2-carboxylic acid, 5-fluoro-2-methoxybenzoic acid, 3-fluorobenzoic acid, 4-fluorobenzoic acid, 3,6-difluoropyridine-2-carboxylic acid, 6-fluoro-2-pyridinecarboxylic acid, 2,3-difluoropyridine-4-carboxylic acid, 2-iodosobenzoic acid, 2-cyanobenzoic acid, 3-cyanobenzoic acid, 4-cyanobenzoic acid, 3-(dimethylamino) benzoic acid, 4-(dimethylamino)benzoic acid, n-methylanthranilic acid, 3-(methylamino)benzoic acid, 4-(methylamino)benzoic acid, ammonium benzoate, 1-methyl-2-pyrrolecarboxylic acid, 1-ethyl-3-methyl-1H-pyrazole-5-carboxylic acid, 1-ethyl-5-methyl-1H-pyrazole-3-carboxylic acid, 4-(1-pyrrolidinyl)benzoic acid, 6-(1-piperidinyl)pyridine-3-carboxylic acid, 4-(4-morpholinyl) benzoic acid, 2,6-dimethoxypyridine-3-carboxylic acid, 3-methylpyridine-2-carboxylic acid, 4-methylpyridine-2-carboxylic acid, 6-m ethoxypyridine-2-carboxylic acid, 3-ethyl-5-methylisoxazole-4-carboxylic acid, 5-isopropyl isoxazole-4-carboxylic acid, 5-isopropylisoxazole-3-carboxylic acid, 5-cyclopropylisoxazole-3-carboxylic acid, 2,1,3-benzoxadiazole-5-carboxylic acid, 4-acetyl-3,5-dimethyl-2-pyrrolecarboxylic acid, 4-methylpyrrole-2-carboxylic acid, indole-3-carboxylic acid, indole-4-carboxylic acid, 1h-benzimidazole-2-carboxylic acid monohydrate, 2-methoxycarbonylamino-1h-benzoimidazole-6-carboxylic acid, 3-isopropylpyrazole-4-carboxylic acid, 3-isopropylpyrazole-5-carboxylic acid, 3-cyclopropylpyrazole-5-carboxylic acid, luf6283, indazole-3-carboxylic acid, 1h-indazole-6-carboxylic acid, 1h-indazole-5-carboxylic acid, 1H-indazole-4-carboxylic acid, benzotriazole-5-carboxylic acid, 2-ethoxybenzoic acid, 3-ethoxybenzoic acid, 4-ethoxybenzoic acid, mono-methyl phthalate, mono-methyl isophthalate, mono-methyl terephthalate, 2,3,4-trim ethoxybenzoic acid, 2,6-dimethoxybenzoic acid, 2,4,5-trimethoxybenzoic acid, 3,4,5-trimethoxybenzoic acid, 2,5-dimethoxybenzoic acid, 3,4-dimethoxybenzoic acid, 2,4-dimethoxybenzoic acid, 2,3-dim ethoxybenzoic acid, 2-m ethoxybenzoic acid, 3,5-dim ethoxybenzoic acid, 3-m ethoxybenzoic acid, 4-m ethoxybenzoic acid, acetylsalicylic acid, 3-acetoxybenzoic acid, 4-acetoxybenzoic acid, 2-acetylbenzoic acid, o-toluic acid, 2-carboxybenzaldehyde, 3-ethynylbenzoic acid, m-toluic acid, 3-formylbenzoic acid, p-toluic acid, 4-formylbenzoic acid, 3-methyl-2-furoic acid, 1,4-benzodioxan-5-carboxylic acid, 1,4-benzodioxane-6-carboxylic acid, piperonylic acid, 7-bromo-2,3-dihydro-[1,4]dioxino[2,3-b]pyridine-8-carboxylic acid, 2-fluoro-6-(pyrrolidin-1-yl)isonicotinic acid, 5-chloro-2-methoxynicotinic acid, 5-chloro-2,3-dimethoxyisonicotinic acid, 4-chloro-pyridine-2-carboxylic acid, 5,6-dimethoxypicolinic acid, 2-chloro-6-methoxynicotinic acid, 2-methoxy-5-methylnicotinic acid, 2-fluoro-6-(pyrrolidin-1-yl)nicotinic acid, 2-methoxy-6-(pyrrolidin-1-yl)nicotinic acid, 1H-pyrrolo[3,2-b]pyridine-6-carboxylic acid, 1H-pyrrolo[3,2-c]pyridine-4-carboxylic acid, 5-methyl-1H-pyrrolo[2,3-b]pyridine-3-carboxylic acid, 5-fluoro-1H-pyrrolo[2,3-b]pyridine-4-carboxylic acid, 5-fluoro-1H-pyrrolo[2,3-b]pyridine-6-carboxylic acid, furo[3,2-b]pyridine-6-carboxylic acid, 3,4-dihydro-2H-pyrano[2,3-b]pyridine-6-carboxylic acid, 7-chloro-2,3-dihydro-[1,4]dioxino[2,3-b]pyridine-8-carboxylic acid, 7-chloro-2,3-dihydro-[1,4]dioxino[2,3-b]pyridine-6-carboxylic acid, 2,5,6-trimethoxynicotinic acid, 3-ethyl-4-methyl-1H-pyrazole-5-carboxylic acid, 2-isopropyl-4-pyrimidinecarboxylic acid, 6-methylimidazo[1,2-a]pyridine-2-carboxylic acid, 3-(1-methyl-1H-pyrrol-2-yl)-1H-pyrazole-5-carboxylic acid, 3-isopropyl-1-methyl-1H-pyrazole-5-carboxylic acid, 2H-1,2,3-benzotriazol-2-ylacetic acid, 3-(3-chloroisoxazol-5-yl) propanoic acid, 5-propyl isoxazole-3-carboxylic acid, 3-propyl-1H-pyrazole-5-carboxylic acid, 6-methoxyhexanoic acid, 5-acetyl-2,4-dimethyl-1H-pyrrole-3-carboxylic acid, 3-methyl-1-propyl-1H-pyrazole-4-carboxylic acid, (8-methylimidazo[1,2-a]pyridin-3-yl)acetic acid hemihydrochloride, 4-(1H-1,2,4-triazol-5-yl)benzoic acid hydrate, 1,5-dimethyl-1H-pyrrole-2-carboxylic acid, 4-ethynylbenzoic acid. It would be clear to a person skilled in the art that the equivalent sulfonic, phosphonic, phosphate and bisulfite acids could be used. R—X can comprise some mixture or combination of the above in different ratios to give a diversity of different structural forms that may better stabilise or improve the hydrophobic interaction between the substituted metal complex and the hydrophobic surface.

In addition, different metal ions can be also be used. Therefore, more than one type of metal complex can be used in the present invention.

The hydrophobic ligand may exclude pentahydroxytetradecanoic acid, tetradecanoic acid, octadecanoic acid, and mixtures thereof.

In another aspect, the present invention relates to a composition including a metal complex, the metal complex including a metal ion, the metal ion having:
  (i) one or more co-ordination sites occupied by a hydrophobic ligand for binding the metal complex to a hydrophobic surface, and
  (ii) one or more co-ordination sites available for binding to a target molecule.

The "composition" for use in, or when used in, the methods of the present invention may be an aqueous or alcoholic solution containing, in addition to the metal complex (i.e. the metal ion and hydrophobic ligand) to be coated onto a substrate or surface, other components such as surfactants, buffers, etc.

Similarly, the degree to which the metal ion is substituted with R—X will affect binding strength to the substrate surface. However, as the invention resides in the fact that two faces of the substituted metal complex need to be present, R—X cannot coordinate to all the available coordination sites of the metal complex. The binding strength of the substituted metal complex is dependent on the selection and number of R groups that are present in the substituted metal complex and the surface properties of the substrate. Polystyrene (PS), cyclic olefin copolymers (COC) or polymers (COP), polyvinylidene fluoride (PVDF), etc, are examples of substrates that have essentially hydrophobic surfaces and are expected to interact predominantly with the R group of the substituted metal complex. There are also other substrates (such as polycarbonate (PC) and polyether sulphone (PES)) that also include some polar species within a largely hydrophobic substrate. Accordingly, the ability to select and control the type and amount of R groups on the substituted metal complexes allows greater tuning and optimisation of the substituted metal complex to bind different substrates and present a chelating surface of desired characteristics. Assuming coordination potential of the metal ion is defined as 100%, the degree to which R—X coordinates with the metal ion can vary from 1 to 99%, but is preferably in the range of about 25 to about 75%. In one embodiment, the degree to which R—X coordinates with the metal ion is from about 25% to about 50%.

As mentioned above, the metal complex binds to the surface such that the co-ordination sites on the metal ion that are available for binding to a target molecule are directed away from the hydrophobic surface. As a consequence, the metal complexes form a surface where the co-ordination sites of the metal ion are oriented relative to the hydrophobic surface such that they form a hydrophilic co-ordinating surface on the hydrophobic surface.

It will be understood by a person skilled in the art that the metal ion may be associated with one or more other co-ordination ligands (in addition to the hydrophobic ligand discussed above). In addition, a "coordination ligand" can include any species that can link transition metal ions together or displace one co-ordination ligand with another. A relevant ligand may also assist or facilitate the oligomerisation of metal oxide species prior to, or on, a substrate surface. For example, a chromium metal oligomer of up to 10 to 12 chromium atoms could be linked with another metal-based oligomer by an appropriate co-ordination ligand. Accordingly, the substrates and surfaces of the present invention can include metal complexes and metal ions in the form of oligomers. In addition, the methods of the present invention can form modified substrates and surfaces having oligomers of metal ions bound thereto.

Examples of suitable ligands include those having an acid or amine-containing group forming a co-ordination bond with the transition metal ion. Examples of ligands that may be used include ethylenediamine, tetramethylethylenediamine, iminodiacetic acid, nitrilotriacetic acid, triphenylphosphine, oxalic acid, 1,10-phenanthroline, 8-hydroxyquinoline, salicylic acid, chloride, acetate, bromide, nitrate, perchlorate, alum, sulphate and pyridine. Ethylenediamine is preferred.

The metal complexes of the present invention therefore contain two distinct binding components. The metal ions have a substantial percentage (but not all) of their chelation potential to bind a ligand already occupied by hydrophobic ligands (R—X) having an R-group and a chelating group (X) as discussed above. The R—X ligand does not bind to the metal ion by the R-group because of the hydrophobic nature of the R-group. The metal ion binds or interacts, via the R-group, with a hydrophobic surface (which may be completely, substantially or partially hydrophobic) on a substrate. In doing so, the modified metal complex forms a coating (via non-covalent and non-coordinative interactions with the surface), which coating may be complete or partial, on the substrate, and presents a metal complex binding face to bind a target molecule.

The interaction between the hydrophobic ligand and the hydrophobic surface is a non-covalent and a non-coordinative interaction. That is, it does not involve the formation of covalent bonds or co-ordination bonds (also known as dative and coordinate covalent bonds). The interaction may be the result of a hydrophobic interaction. The interaction may also be a result of electrostatic effects (e.g. ionic, hydrogen bonding and halogen bonding), $\pi$-effects (e.g. $\pi$-p interactions, cation-$\pi$ and anion-$\pi$ interactions, polar $\pi$ interactions) and/or van der Waals forces (dipole-dipole, dipole-induced dipole and London dispersion forces). It will be understood by a person skilled in the art that the interaction may also be a combination of hydrophobic effects, electrostatic effects, $\pi$-effects and/or van der Waals forces.

It will be clear to a person skilled in the art that the metal complex may be associated with a counter-ion (such as chloride, acetate, bromide, nitrate, perchlorate, alum, fluoride, formate and sulphate), which can be co-ordinating or non-coordinating. The metal complexes can be formed under various conditions including the use of solvents such as water, ethanol, methanol, isopropanol, n-pentanol, lower alcohols, polyhydric alcohols, lower ketones, dioxane, tetrahydrofuran and carbon tetrachloride, and the use of bases, such as potassium hydroxide, sodium bicarbonate, sodium sulphite and ammonia. Depending on the solvent, the concentration of different substituted metal complexes, the presence of other ligands that may temporarily chelate to the substituted metal complex, as well as the conditions under which such metal complexes may or may not oligomerise with each other, all affect the efficiency of binding to substrate.

In another aspect, the present invention relates to a method of modifying a hydrophobic surface, the method including:
  providing a surface that is hydrophobic,
  contacting the surface with a metal complex, the metal complex including a metal ion having:
    (i) one or more co-ordination sites occupied by a hydrophobic ligand for binding the metal complex to the hydrophobic surface, and
    (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface,
thereby forming a surface having increased hydrophilicity.

In another aspect, the present invention relates to a method of treating an at least partially hydrophobic surface to increase its hydrophilicity, the method including:
  providing a surface that is hydrophobic
  contacting the surface with a metal complex, the metal complex including a metal ion having:
    (i) one or more co-ordination sites occupied by a hydrophobic ligand for binding the metal complex to the hydrophobic surface, and
    (ii) one or more co-ordination sites available for binding to a target molecule,
wherein the hydrophobic ligand binds to the hydrophobic surface by non-covalent and non-coordinative interactions such that the co-ordination sites available for binding to a target molecule are directed away from the hydrophobic surface,
thereby forming a surface having increased hydrophilicity.

The methods discussed herein may include the further step of contacting the treated surface with a target molecule for binding the target molecule to the surface.

In another aspect, the present invention relates to a method for binding a target molecule to a substrate, the method including:
  providing a substrate having a surface that is hydrophobic,
  contacting the surface with a metal complex, the metal complex including a metal ion having:
    (i) one or more co-ordination sites occupied by a hydrophobic ligand for binding the metal complex to the hydrophobic surface, and
    (ii) one or more co-ordination sites available for binding to a target molecule,
wherein the hydrophobic ligand binds to the hydrophobic surface by non-covalent and non-coordinative interactions such the co-ordination sites available for binding to a target molecule are directed away from the hydrophobic surface,
  contacting a target molecule with the metal complex, thereby binding the target molecule to the substrate.

In another aspect, the present invention relates to a metal complex for use in, or when used in, the methods of the present invention.

In another aspect, the present invention relates to a composition including a metal complex for use in, or when used in, the methods of the present invention.

In all of the aspects discussed herein, the metal complexes may partially coat the substrate, thereby providing the substrate with coated and uncoated surface regions, or the complexes may completely coat the substrate, thereby enclosing or covering the substrate within the layer of metal complexes. In this way, the properties of the substrate, as affected by the layer, can be controlled. For example, a full coating layer may prevent the substrate from degrading and may also serve to protect the surrounding environment (for example, where the substrate is used in vivo and is toxic) from materials within the substrate. However, where unmodified regions of the substrate are desired (for example, forming hydrophilic channels surrounded by unmodified "hydrophobic" regions), only the desired regions of the substrate need to be coated. In another example, such coatings may have the potential to create unique spectral changes in the properties of quantum dots that may actually enhance their properties for some applications (Sadeghi, S. M., Nejat, A, West, R. G. (2012) "Inhibition of plasmonically enhanced interdot energy transfer in quantum dot solids via photo-oxidation", *J. Applied Physics* 112; 104302). As mentioned above, existing methods such as sputter coating to create metal films are hard to control requiring specialised equipment and do not have the potential of creating a diversity of different coatings on nanoparticles.

Preferably, the coating layer formed on a particle, in accordance with the present invention, has a thickness of between about 50% to about 0.1% of the diameter of the particle. Preferably, the coating layer has a thickness of not more than about 50% of diameter of the particle, and, in some cases, not more than about 25% of the diameter of the particle. The coating layer may have a thickness of not more than about 15% of the diameter of the particle (for example, not more than about 10% of the diameter of the particle, and even not more than about 5% of the diameter of the particle). In some embodiments, the coating layer may have a thickness of not more than about 1% of the diameter of the particle.

The coating layer preferably has a thickness of between about 2 and about 10 nm. Preferably, the thickness of the coating layer is not more than about 10 nm, more preferably not more than about 5 nm, and even more preferably not more than about 2 nm.

In another aspect, the present invention relates to a particle, the particle including:
- a surface that is hydrophobic, and
- a metal complex including a metal ion, the metal ion having:
  (i) one or more co-ordination sites occupied by a hydrophobic ligand for binding the metal complex to the hydrophobic surface, and
  (ii) one or more co-ordination sites available for binding to a target molecule, wherein the hydrophobic ligand binds to the hydrophobic surface by non-covalent and non-coordinative interactions such the co-ordination sites available for binding to a target molecule are directed away from the hydrophobic surface.

In another aspect, the present invention relates to a composition including the particle of the present invention.

In addition to the benefits discussed above (e.g. improving or maintaining the existing bulk properties of a substrate, protecting and preventing the substrate from being contaminated or damaged by, as well as from contaminating or damaging, the surrounding environment) the coating layer also maintains the morphology of the substrate and provides a consistent and uniform surface for binding target molecules thereon. All of these advantages are particularly important in the context of particle coatings, but also apply to planar or flat substrates.

A substrate may also be formed having regions of different metal complexes. This could be achieved by, for example, masking a portion of the surface, coating the surface with one type of metal complex, unmasking the other regions and coating the unmasked regions with another type of metal complex. In this way, a substrate having "controlled regions" can be formed.

As discussed above, substrate surfaces may include both hydrophilic and hydrophobic regions, as a result of, for example, the methods by which the substrates are formed and treated. On such substrate surfaces it is possible that coordination via metal complexes can occur and result in a hydrophobic coating instead of the preferred hydrophilic surface coating. In such a system both hydrophobic interaction and coordination via metal complexes is occurring and to avoid formation of such mixed surfaces, combinations of metal complexes can be used. For example, metal complexes as disclosed in WO 2006/002472 can be used to coat substrate surface regions having chelating potential (hydrophilic regions) leaving hydrophobic regions uncoated. Subsequently, the substituted metal complex incorporating hydrophobic ligands can bind and coat the remaining hydrophobic regions to form a metal complex surface of greater uniformity to bind target molecule. Such combinations of metal complexes can be selected according to the characteristics of the substrate.

Depending on the method used to manufacture them, or treatments or conditions to which they may be exposed, even hydrophilic substrates such as glass or metal oxides may vary in the presence of surface oxygen and other polar species and lead to non-uniform surface regions that vary in hydrophobicity. In the case of particles used in life science applications such as immunoassays, such hydrophobic regions are thought to be the cause of non-specific binding (NSB) leading to poor assay performance. The use of different types of metal complexes (e.g. those disclosed in WO 2006/002472 and the complexes of the present invention) results in greater surface uniformity of coating to bind target molecules across the whole surface, when compared to the use of just one metal complex coating.

The present invention also relates to post-coating treatments to achieve greater uniformity of a metal complex surface to coordinate target molecules. Greater substitution of available coordination sites on the metal ion with a hydrophobic ligand can improve binding to hydrophobic substrates but decreases available coordination sites to bind target molecules and potentially renders the metal complex useless for the purposes of the invention. It is desirable to adjust the ratio of ligand to the metal ion, the combinations of different R-groups and ratios to the substrate to achieve optimal binding of target molecules. pH and temperature can also be used to stabilise and further improve surface uniformity of the coated surface to coordinate and bind target molecules.

It is known that post-coating treatments will allow coordination between different metal complexes to form larger oligomeric metal complexes on the substrate surface. Similarly, a target molecule comprising any multi-dentate ligand, whether biological (such as polynucleotides, proteins, peptides, polysaccharides, etc) or synthetic macromolecules (such as polyvinylalcohol, polyacrylic acid, glycidyl methacrylate, nanoparticles, etc) also has the potential to form cross-links between the metal complexes already anchored to the substrate. In either case, cross-linking by co-ordination bonds with two or more transition metal ions or transition metal ion oligomers, thereby linking a transition metal ion to another transition metal ion, a transition metal ion to an oligomer, or an oligomer to another oligomer, can be achieved. Methods of forming oligomers from metal complexes are discussed in WO 2011/140590.

The metal complexes used in the invention give very thin films in nanometre dimensions that may still expose the underlying characteristics of the substrate even though there are now available metal complexes on its surface. In such a situation, the metal complex can further form co-ordination complexes with other multi-dentate ligands (e.g. proteins, polynucleotides, carbohydrates, lipids, drugs, labelling agents, synthetic polymers, further particles, such as a nano- and microparticles, and biological particles, as discussed above) and, by treatment with more metal complexes, create further complex coating structures. By such methods, very thin films of different thicknesses, density, hydrophobicity, hydrophilicity, or charge can be produced without compromising colloidal stability in the case of particles and other examples.

In all of the embodiments of the present invention, it will be understood that, but for the presence of the "R" group in the metal complex, the coating layer would not be bound to the substrate. It is the "R" group, via hydrophobic or other non-covalent and non-coordinative interactions with the substrate, that effectively binds the metal ion layer to the substrate. The remaining co-ordination bonds on the metal ion are left available for binding target molecules to give a target molecule bound to a substrate. In binding a target molecule to the metal complex surface, the mechanism is believed to involve an initial charge interaction followed by chelation, which is often irreversible or tuned for reversibility.

The metal complex coatings may also form a functionalised surface, thereby facilitating the formation of surface groups used in conventional binding methods such as carboxylic acids and epoxy groups, or a surface for further modification by the use of metal complexes to:
- modify the surface properties of a substrate,
- improve or maintain the stability of the existing bulk properties of a substrate,
- protect and prevent the bulk properties of a substrate from contaminating or damaging the surrounding environment, and
- modify or manipulate the existing bulk properties of a substrate to create a different substrate having properties that are different from the original.

The present invention will be described with particular reference to forming coatings on polystyrene (PS) and cyclic olefin copolymers (COC) microtitre plates to bind target molecules. However, it will be appreciated that the underlying concepts of the invention are applicable to any substrate surface used, and not limited to, in vitro diagnostics and in vivo imaging, drug delivery, drug discovery, bioprocessing, enzyme-mediated chemical reactions, as well as non-life science applications such as electronics and catalysis, where barrier coatings are required to maintain the pre-existing properties of a substrate. In addition, the potential to form a diversity of different coatings to bind essentially any substrate surface to present a common chelating surface to bind target molecules has further benefits as a discovery tool in identifying potentially useful attributes as a consequence of such coatings. The present invention relates to an alternative approach to forming binding surfaces for target molecules. This approach is believed to afford increased simplicity and reproducibility in forming useful coatings of benefit on different substrates in the various applications described above.

It will be understood that the invention disclosed and defined in this specification extends to all alternative combinations of two or more of the individual features mentioned or evident from the text or drawings. All of these different combinations constitute various alternative aspects and embodiments of the invention.

EXAMPLES

Example 1: Assembly of Metal-Hydrophobic Ligand Complexes (Chromium Chloride Salts with Aliphatic Acids)

A. Mole Proportion:Chromium/Stearic Acid=2/1.

To a solution of 44.48 g of chromic chloride hexahydrate in 100 mL of isopropyl alcohol 10.63 g of finely pulverized potassium hydroxide was added slowly with stirring. This mixture was allowed to stir for 10 minutes at room temperature after which 23.99 g of stearic acid was added slowly while stirring and then further diluted by another 100 mL of isopropyl alcohol. The resultant mixture was subsequently brought to reflux and maintained at such for 30 minutes. The reaction was then cooled to room temperature and filtered to obtain a dark green water-soluble coordination complex chromic salt.

B. Mole Proportion:Chromium/Stearic Acid=4/1.

To a solution of 44.42 g of chromic chloride hexahydrate in 100 mL of isopropyl alcohol 7.93 g of finely pulverized potassium hydroxide was added with stirring. This mixture was allowed to stir for 10 minutes at room temperature after which 12.0 g of stearic acid was added while stirring. Another 100 mL of isopropyl alcohol was then added and the resultant mixture was then gently brought to reflux and refluxed for 30 minutes to obtain a dark green water-soluble coordination complex chromic salt. The reaction mixture was cooled to room temperature and filtered.

C. Mole Proportion:Chromium/Hexanoic Acid=4/1.

To a solution of 5.02 mL of hexanoic acid in 50 ml of isopropyl alcohol 7.93 g of finely ground potassium hydroxide was added slowly with stirring. This mixture was allowed to stir for 10 minutes at room temperature after which 44.41 g of chromium chloride hexahydrate in 150 mL of isopropyl alcohol was added dropwise while stirring. The resultant mixture was then gently brought to reflux and maintained at reflux for 30 minutes to obtain a dark green water-soluble coordination complex chromic salt. This solution was cooled to room temperature and filtered.

D. Mole Proportion:Chromium/Sodium Butyrate=2/1.

To a solution of 4.403 g of sodium butyrate in 100 mL of isopropyl alcohol 8.98 g of finely pulverized potassium hydroxide and 44.423 g of chromic chloride hexahydrate wasere added slowly with stirring and a further addition of 100 mL of isopropyl alcohol. The resultant mixture was then gently brought to reflux and maintained at such for 30 minutes to obtain a dark green water-soluble coordination complex chromic salt. This solution was cooled to room temperature and filtered to obtain a solution that was miscible with water and behaved in a similar manner to the other solutions in Example 1.

Example 2: Assembly of Metal-Hydrophobic Ligand Complexes (Alternative Salts with Aliphatic Acids)

A. Mole Proportion:Chromium/Lauric Acid=4/1.

To a solution of 64.67 g of chromic nitrate nonahydrate in 100 mL of isopropyl alcohol 7.923 g of finely pulverized potassium hydroxide was added slowly with stirring. This mixture was allowed to stir for 10 minutes at room temperature after which 8.18 g of lauric acid was added slowly with stirring and then further diluted by another 100 mL of isopropyl alcohol. The resultant mixture was subsequently brought to reflux and maintained at such for 30 minutes. The reaction was then cooled to room temperature and filtered to obtain a dark blue water-soluble coordination complex chromic salt.

Similarly, any other chromium salts can be used to form these substituted metal complexes.

Example 3: Assembly of metal-hydrophobic ligand complexes (with aromatic acids)

A. Mole Proportion:Chromium/Benzoic Acid=2/1.

To a solution of 44.42 g of chromic chloride hexahydrate in 100 mL of isopropyl alcohol 10.568 g of finely ground potassium hydroxide was added slowly with stirring. This mixture was allowed to stir for 10 minutes at room temperature after which 9.82 g of benzoic acid was added slowly while stirring and then further diluted by another 100 mL of isopropyl alcohol. The resultant mixture was subsequently brought to reflux and maintained at such for 30 minutes. The reaction was then cooled to room temperature and filtered to obtain a dark green water-soluble coordination complex chromic salt.

B. Mole Proportion:Chromium/1-Naphthoic Acid=4/1.

To a solution of 43.53 g of chromic chloride hexahydrate in 100 mL of isopropyl alcohol 7.93 g of finely pulverized potassium hydroxide was added slowly whilst stirring. This mixture was allowed to stir for 10 minutes at room temperature after which 7.05 g of 1-naphthoic acid was added slowly while stirring and then a further addition of 100 mL of isopropyl alcohol. The resultant mixture was subsequently brought to reflux and maintained at such for 30 minutes. The reaction was then cooled to room temperature and filtered to obtain a dark green water-soluble coordination complex chromic salt.

Example 4: Assembly of Metal-Hydrophobic Ligand Complexes (Other Substitutions)

A. Mole Proportion:Chromium/Malonic Acid=2/1.

To a solution of 10.71 g of malonic acid in 100 mL of ethanol 13.21 g of potassium hydroxide was added with stirring resulting in a white suspension. This white suspension was allowed to stir for 15 minutes at room temperature after which 55.52 g of chromium chloride hexahydrate was added with stirring. The resultant dark green mixture was then gently brought to reflux and refluxed for 15 minutes to obtain a dark green soluble chromic salt. This mixture was centrifuged at 10 000 rpm for 10 minutes. The dark green supernatant was then decanted from the off-white pellet.

B. Mole Proportion:Chromium/Sorbic Acid=4/1.

To a solution of 44.44 g of chromic chloride hexahydrate in 100 mL of isopropyl alcohol 7.93 g of potassium hydroxide was added with stirring. This mixture was allowed to stir for 10 minutes at room temperature after which 4.581 g of sorbic acid and 100 mL of isopropyl alcohol was added while stirring. The resultant mixture was then gently brought to reflux and refluxed for 30 minutes to obtain a dark green water-soluble chromic salt. This mixture was centrifuged at 10 000 rpm for 10 minutes. The dark green supernatant was then decanted from the off-white pellet.

Example 5: Assembly of Metal-Hydrophobic Ligand Complexes (Mixed Substitutions)

A. Mole Proportion:Chromium/Mixed Acids=2/1.

To a solution of 72.05 g of chromic nitrate nonahydrate in 100 mL of isopropyl alcohol 11.91 g of potassium hydroxide was added with stirring. This mixture was allowed to stir for 10 minutes at room temperature after which 6.13 g of lauric acid, 3.69 g of benzoic acid and 6.07 g of biphenyl-4-carboxylic acid and 100 mL of isopropyl alcohol was added with stirring. The resultant mixture was then gently brought to reflux and maintained at that temperature for 30 minutes to obtain a dark blue, water-soluble chromic salt. After cooling to room temperature the mixture was centrifuged at 10 000 rpm for 10 minutes. The dark blue supernatant was then decanted from the off-white pellet.

Example 6: Assembly of Metal-Hydrophobic Ligand Complexes

Similar formulations can be been prepared by the addition of carboxylic, sulphonic and phosphonic alkali metal salts to different chromium salts such as $Cl^-$, $NO_3^-$, $SO_4^{2-}$, $F^-$, $Br^-$, $HCOO^-$, $H_3COO^-$, and any other counter-ion. The above procedures can be performed in other solvents such as EtOH, MeOH, n-pentanol, lower alcohols, polyhydric alcohols, lower ketones, dioxane, tetrahydrofuran and carbon tetrachloride. As well, many alternative bases such as KOH, $NaHCO_3$, $Na_2SO_3$ and $NH_3$ can also be used in the invention.

Alternatively, metal complex formulations as disclosed in WO 2006/002472 and WO 2011/140590 can be first produced and similar substituted metal complexes can be prepared by the addition of carboxylic, sulphonic and phosphonic alkali metal salts in appropriate molar ratios with respect to the metal ion of between 1:4 to 1:1, with stirring.

Example 7: Contact Angle Studies on Substrates

A. On PS Surfaces

A 20 μL drop of milliQ water was deposited onto the surface of an untreated PS slide giving a high contact angle. PS Slides were treated according to the dip coat method by standing in a 100 mM solution of metal-hydrophobic ligand complexes (from Example 5A and Example 2A) for 1 hour, removed from the solution and allowed to air dry. The surface was left for another hour at 37° C. A 20 μL drop of water was then applied to two different treated surfaces. The contact angle θ was observably lowered. This is depicted in FIGS. 1 B (Example 5A) and C (Example 2A).

B. On COC Surfaces

Figure 2:
FIG. 2. A. Contact angle of untreated COC surfaces, B. Contact angle of treated (1) COC surface (treated with the metal-hydrophobic ligand complex of Example 2A), C. Contact angle of treated (2) COC surface (treated with the metal-hydrophobic ligand complex of Example 5A).
Figure 2:
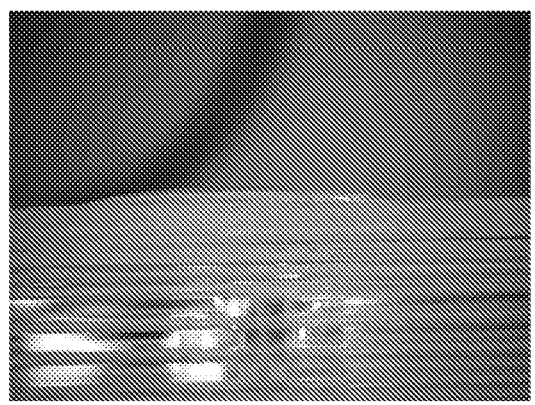
Figure 2:
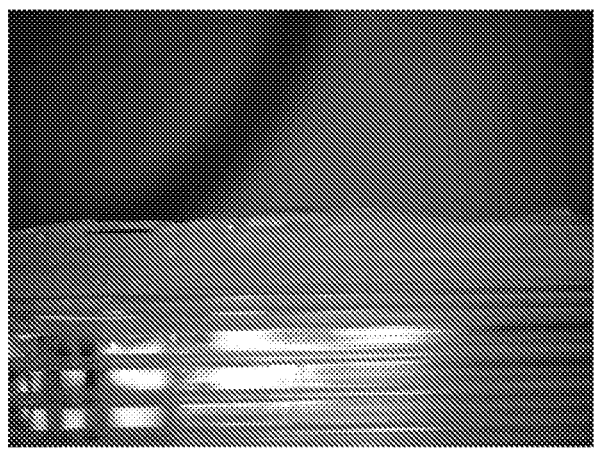

A 20 μl drop of milliQ water was deposited onto the surface of an untreated COC slide giving a high contact angle. COC Slides were treated according to the dip coat method by standing in a 100 mM metal-hydrophobic ligand complexes (Example 2A and Example 5A) for 1 hour, removed from the solution and allowed to air dry. The surface was left for another hour at 37° C. A 20 μL drop of water was then applied to two different treated surfaces. The contact angle θ was observably lowered. This is depicted in FIGS. 2 B (Example 2A) and C (Example 5A).

Example 8: Forming a Similar Surface on Different Materials

Four different slides produced from different materials: polystyrene (PS), cyclic olefin copolymer (COC), polycarbonate (PC) and polyethylene terephthalate-glycol (PETG) were treated for one hour at room temperature with 10 mM substituted metal complexes (chromium chloride version of procedure used in Example 5) in isopropanol/water (1:1), left in water solution for 1 hr before immersing the activated surface in polyvinylalcohol (PVA) in water (5 mg/mL, 98 kD) for another hour. After washing in water for 1 hr, the excess water was removed from the slides using absorbent paper, left to dry for 30 min, then at 37° C. for another 30 mins in dry box before leaving overnight in dry box.

A 1 µL drop of milliQ water was deposited onto the surface of both untreated and PVA treated slides to calculate contact angle. Five replicates were performed for each surface to obtain average change in contact angle. After treatment with metal complex, the PVA coating was stable even after 24 hr washing. However, without this metal complex, the PVA coating was not stable and washed off to obtain a contact angle similar to the untreated material.

TABLE 1

Contact angle of polyvinyl alcohol (PVA) coated metal complex-activated slides from different materials.

| Material | Contact Angle (°) | After wash & dried | % CV |
|---|---|---|---|
| Polystyrene (PS) | 91 | 53 ± 5 | 9% |
| Cyclic Olefin (COC) | 96 | 50 ± 5 | 11% |
| Polycarbonate (PC) | 82 | 58 ± 5 | 8% |
| Polyethylene terephthalate-glycol (PETG) | 72 | 54 ± 2 | 8% |

These coating studies demonstrate that on different hydrophobic materials, it is possible to form a stable hydrophilic coating using metal complexes as a primer to strongly bind a synthetic polymer such as polyvinyl alcohol and form a polyvinyl alcohol surface.

Example 9: ELISA on PS Microtitre Plates (Antibody Binding

Figure 3:
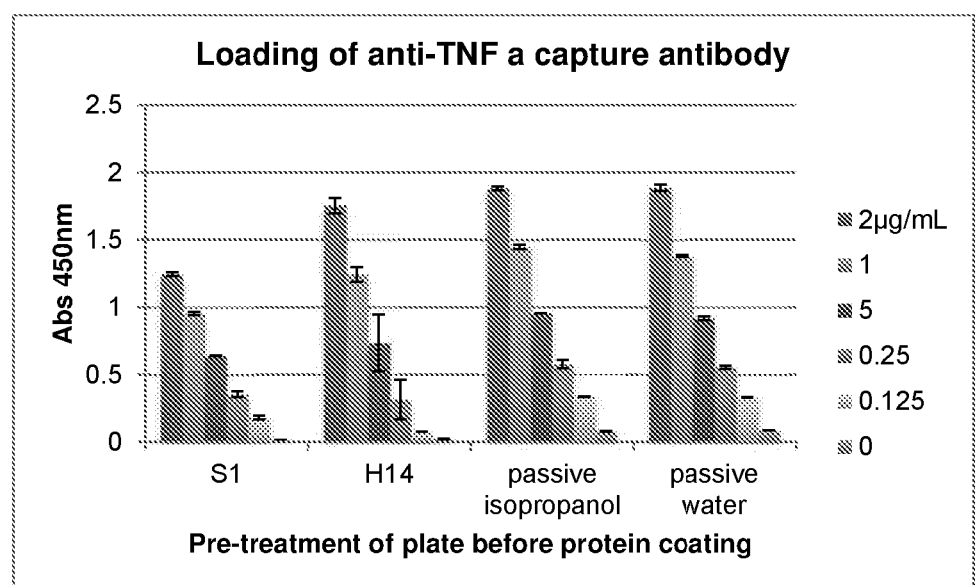
FIG. 3. Antibody loading on PS plates following pre-treatments with two different substituted metal complexes (chromium-lauric acid 4:1 (H14), and chromium-sorbic acid=4:1 (S1).
Figure 4:
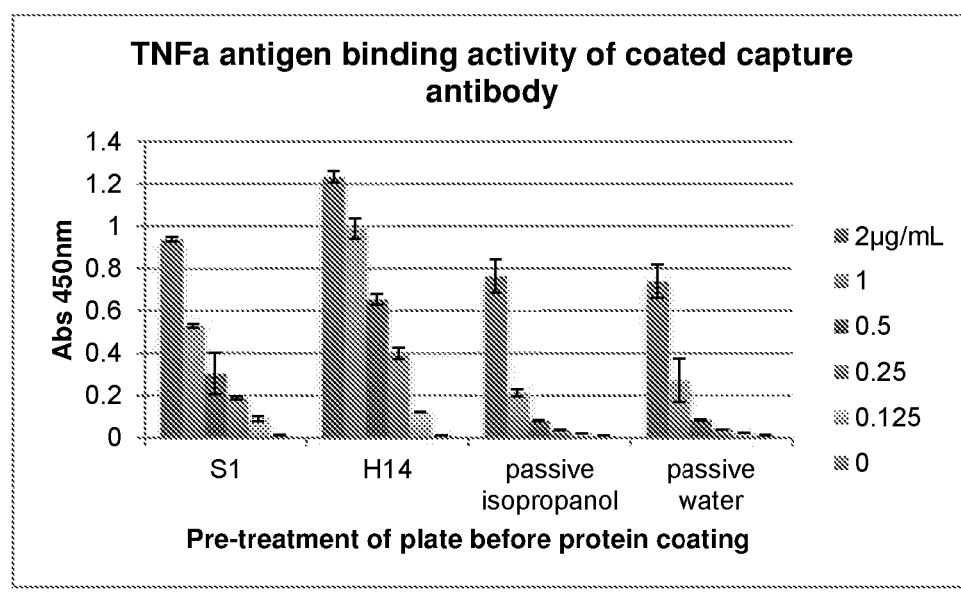
FIG. 4. Antigen binding capacity of antibody coated onto PS plates after pre-treatments with two different metal-hydrophobic ligand complexes (chromium-lauric acid 4:1 (H14), and chromium-sorbic acid=4:1 (S1).

Different polystyrene microtitre plates were treated for one hour at room temperature with various concentrations of metal-hydrophobic ligand complexes in various solvents for protein binding studies. The metal-hydrophobic ligand complexes used were chromium perchlorate with lauric acid (4:1) (referred to as "H14" in FIGS. 3 and 4) and Example 4B (i.e. chromium with sorbic acid (4:1), referred to as "(S1)" in FIGS. 3 and 4). This solution was then aspirated. These plates were dried at 45° C. for an hour then stored in a low humidity chamber at room temperature until use. In this antibody binding study, Low Bind polystyrene plates (Greiner bio-one Cat#655101) were used with 10 mM solutions of the two different metal-hydrophobic ligand complexes in isopropanol.

The capture antibody anti-TNFα (BD Pharmingen Cat#551220) was diluted to 2, 1, 0.5, 0.25 and 0.125 µg/mL in 100 mM carbonate buffer pH 9.6 (100 µL/well) and added to the metal complex treated wells and untreated wells (passive binding). The antibody was incubated for an hour at room temperature on the treated and untreated wells. Plates were then washed once with wash buffer before being blocked with 200 µL/well of 2.5% BSA (AusGenex Cat# PBSA-500 g), in PBS for one hour at room temperature. After blocking the plates were immediately assayed for antibody loading and activity.

Capture antibody loading was determined with direct detection of bound antibody using goat anti-mouse HRP (Jackson Immunoresearch Cat#115-035-003). Conjugate was diluted in assay buffer to a final concentration of 0.1 µg/mL. Plates were incubated for thirty minutes at room temperature before washing. TMB substrate was then added and allowed to react for five minutes before the reaction was stopped with the addition of 100 µL of 2 M sulphuric acid and absorbance read at 450 nm with a background reference of 620 nm.

Capture antibody activity was assessed using an antigen capture assay. A bulk solution of recombinant TNFα (BD Pharmingen Cat#554618) diluted in assay buffer was used at 1 ng/mL across all plates. Antigen was incubated for one hour at room temperature before washing. Captured antigen was detected with biotinylated anti-TNFα antibody (BD Pharmingen Cat#554511) diluted to 1 µg/mL in assay buffer. The biotinylated antibody was incubated at room temperature for thirty minutes before washing. Streptavidin-HRP (Sigma Cat#55512) at 0.1 µg/mL in assay buffer was used to detect bound biotinylated antibody. HRP conjugate was incubated at room temperature for fifteen minutes before washing. Bound conjugate was detected with TMB as described in the antibody loading assay.

These assays demonstrated that although more capture antibody was bound to the plate with passive binding (FIG. 3), the activity of antibody on metal-hydrophobic ligand complex-activated plates (FIG. 4) was two to four times greater than passively-coated plates. The disparity was greater for lower concentrations of capture antibody.

Example 10: ELISA on PS Microtitre Plates (Streptavidin Binding

Different polystyrene microtitre plates were treated for one hour at room temperature with various concentrations of metal-hydrophobic ligand complexes in various solvents for protein binding studies. The metal complexes used were those produced in Example 1C (i.e. chromium with hexanoic acid (4:1), referred to as "H9" in FIG. 5) and Example 2A (i.e. chromium with lauric acid (4:1), referred to as "H13" in FIG. 5). This solution was then aspirated and used immediately. In this streptavidin binding study, Medium bind polystyrene plates (Corning Cat# EIA Costar 2593) were used with 10 mM solutions of the two different metal-hydrophobic ligand complexes in water.

Streptavidin (Prozyme Cat# SA10) was diluted in 100 mM carbonate buffer pH 9.6 to 1.25 µg/mL. One hundred microliters was added to each well and allowed to bind for two hours at room temperature. Plates were then washed once with wash buffer (PBS and 0.1% tween 20), followed by blocking with 200 µL of 1% BSA (AusGenex Cat# PBSA-500 g), 2.5% sucrose in PBS for one hour at room temperature. Blocker was then aspirated from plates and plates dried overnight in a desiccant chamber.

All assays were performed with one hundred microliters of reagent loaded per well. Reagents were diluted in 1% BSA(AusGenex Cat# PBSA-500 g) in PBS (assay buffer). Unless otherwise stated plates were washed five times with wash buffer between each reagent addition.

Activity of bound streptavidin was determined with biotinylated mouse IgG (Jackson Immunoresearch Cat#015-060-003) at the following concentrations, 1, 0.5, 0.25, 0.1, 0 µg/mL in assay buffer. Biotin-mouse IgG was incubated at room temperature for thirty minutes before washing. Bound biotin-mouse-IgG was detected with goat anti-mouse HRP (Jackson Immunoresearch Cat#115-035-003) at 0.1 µg/mL. It was incubated at room temperature for thirty minutes at room temperature, followed by washing. Bound HRP conjugate was detected with tetramethylbenzidine (TMB Thermo scientific Cat #34021) incubated at room temperature for five minutes. The reaction was stopped with 2M sulphuric acid. Absorbance was read at 450 nm (background reference 620 nm).

Figure 5:
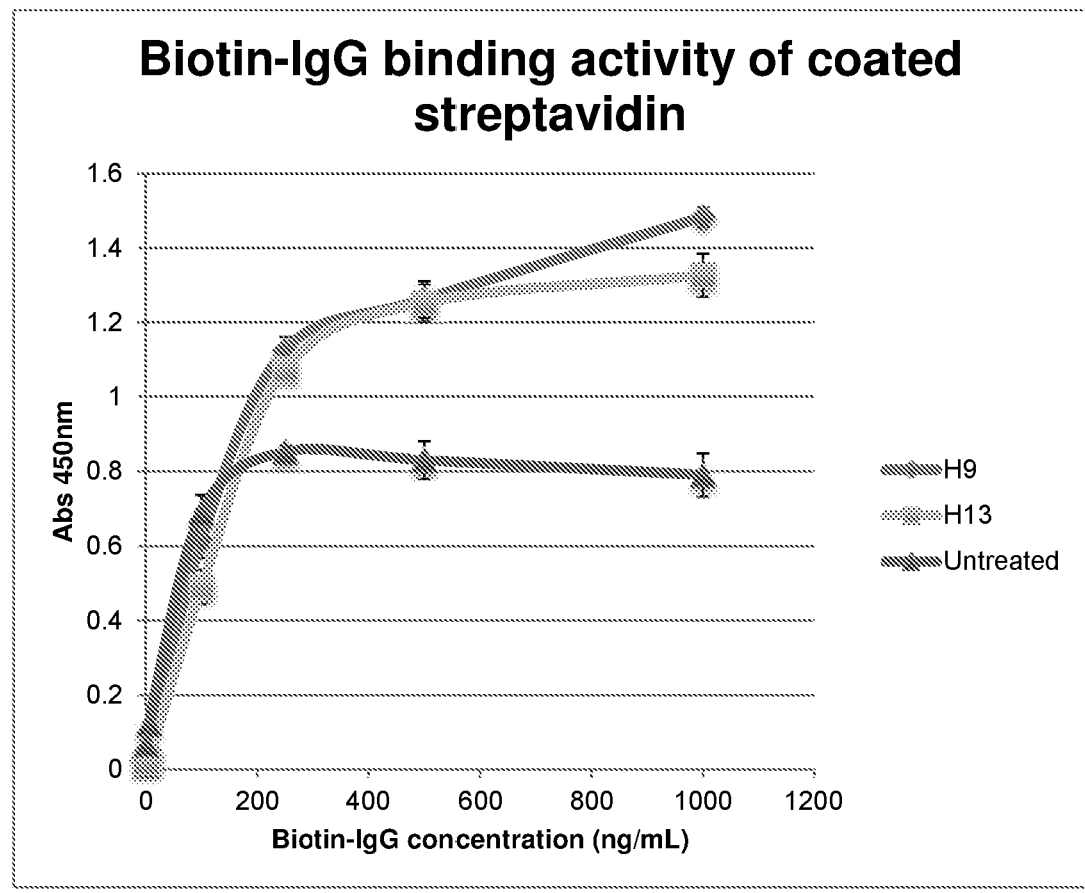
FIG. 5. Activity of streptavidin bound to medium bind PS plates, comparison of two metal-hydrophobic ligand complex-activated plates compared to untreated (passively bound) plates (H9:chromium-hexanoic acid=4:1; H13:chromium-lauric acid 4:1).

FIG. 5 indicates that pre-treatment of medium bind PS surfaces with metal-hydrophobic ligand complexes increased the signal to noise and possibly dynamic range of streptavidin biotin-IgG binding compared to passively coated streptavidin.

Example 11: ELISA on COC Microtitre Plates (Antibody Binding

In this antibody binding study, microtitre plates produced from COC (Greiner Cat #655801) were used with 10 mM solutions (in isopropanol) of a metal-hydrophobic ligand complex produced from chromic chloride with 25% biphenyl carboxylic acid.

The capture antibody anti-TNFα (BD Pharmingen Cat[#]551220) was diluted to 2, 1, 0.5, 0.25 and 0.125 μg/mL in 100 mM carbonate buffer pH9.6 (100 μL/well) and added to the metal complex treated wells and untreated wells (passive binding). The antibody was incubated for an hour at room temperature on the treated and untreated wells. Plates were then washed once with wash buffer before being blocked with 200 μL/well of 2.5% BSA (AusGenex Cat[#] PBSA-500 g), in PBS for one hour at room temperature. After blocking the plates were immediately assayed for antibody loading and activity Capture antibody loading was determined with direct detection of bound antibody using goat anti-mouse HRP (Jackson Immunoresearch Cat[#]115-035-003). Conjugate was diluted in assay buffer to a final concentration of 0.1 μg/mL. Plates were incubated for thirty minutes at room temperature before washing. TMB substrate was then added and allowed to react for five minutes before the reaction was stopped with the addition of 100 μL of 2 M sulphuric acid and absorbance read at 450 nm with a background reference of 620 nm.

Capture antibody activity was assessed using an antigen capture assay. A bulk solution of recombinant TNFα (BD Pharmingen Cat[#]554618) diluted in assay buffer was used at 1 ng/mL across all plates. Antigen was incubated for one hour at room temperature before washing. Captured antigen was detected with biotinylated anti-TNFα antibody (BD Pharmingen Cat[#]554511) diluted to 1 μg/mL in assay buffer. The biotinylated antibody was incubated at room temperature for thirty minutes before washing. Streptavidin-HRP (Sigma Cat[#]55512) at 0.1 μg/mL in assay buffer was used to detect bound biotinylated antibody. HRP conjugate was incubated at room temperature for fifteen minutes before washing. Bound conjugate was detected with TMB as described in the antibody loading assay.

Figure 6:
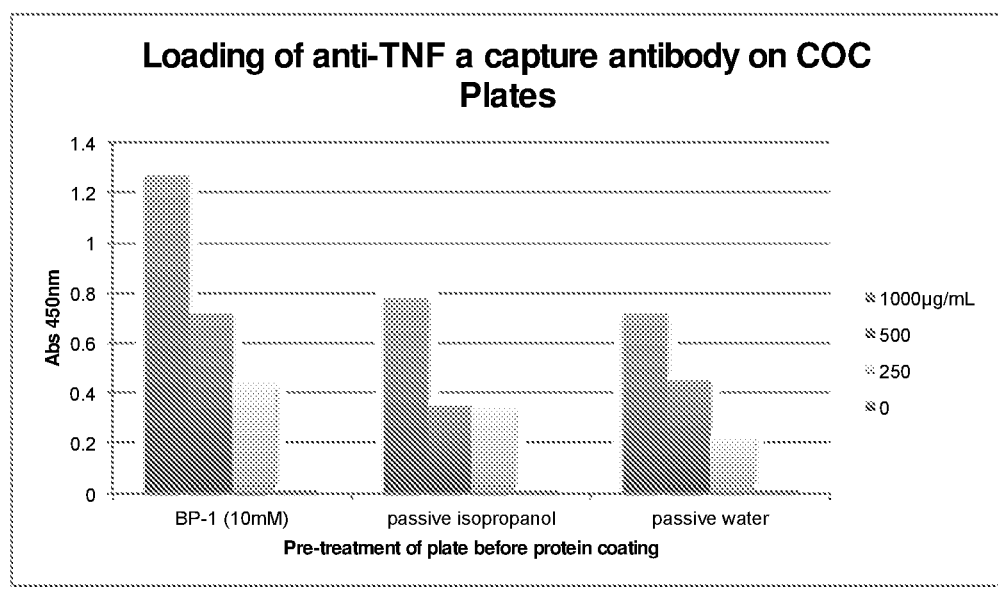
FIG. 6. Antibody loading on COC plates following pre-treatment with metal-hydrophobic ligand complex (BP-1: chromium-biphenyl carboxylic acid=4:1).
Figure 7:
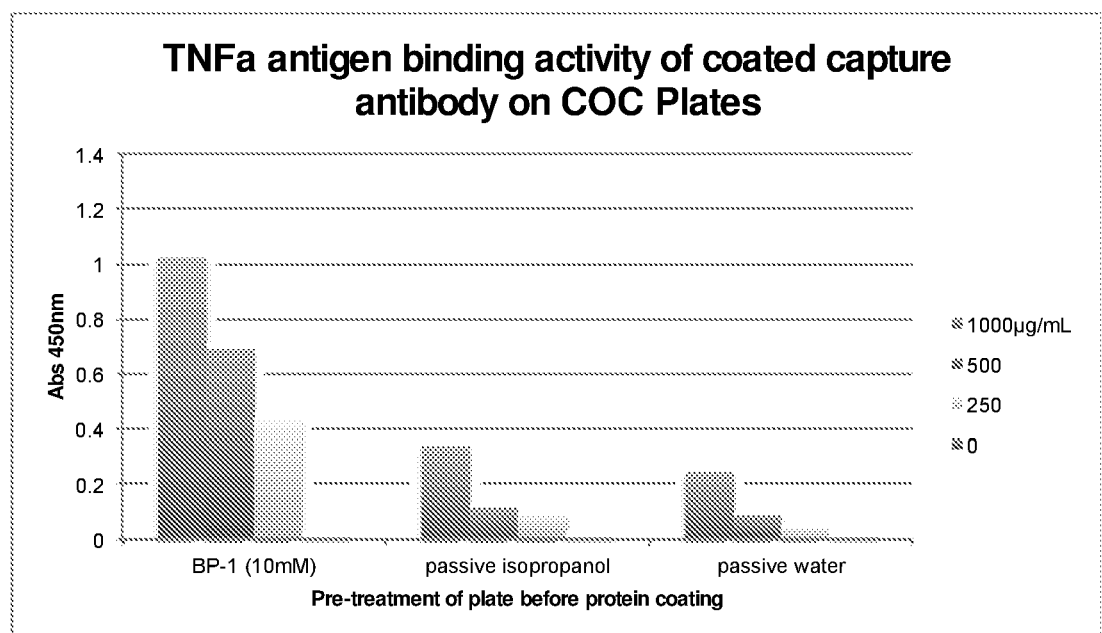
FIG. 7. Antigen binding capacity of antibody coated onto COC plates after pre-treatment with metal-hydrophobic ligand complex (BP-1).

These assays demonstrated that more capture antibody was bound to metal-hydrophobic complex-activated (chromium perchlorate with biphenyl carboxylic acid (4:1), "BP-1") COC plates compared to passive binding (FIG. 6), and the activity of antibody on metal-hydrophobic ligand complex-activated plates (FIG. 7) was significantly greater than passively-coated plates. The disparity was greater for lower concentrations of capture antibody.

Example 12: ELISA on COC Microtitre Plates (Streptavidin Binding

Figure 8:
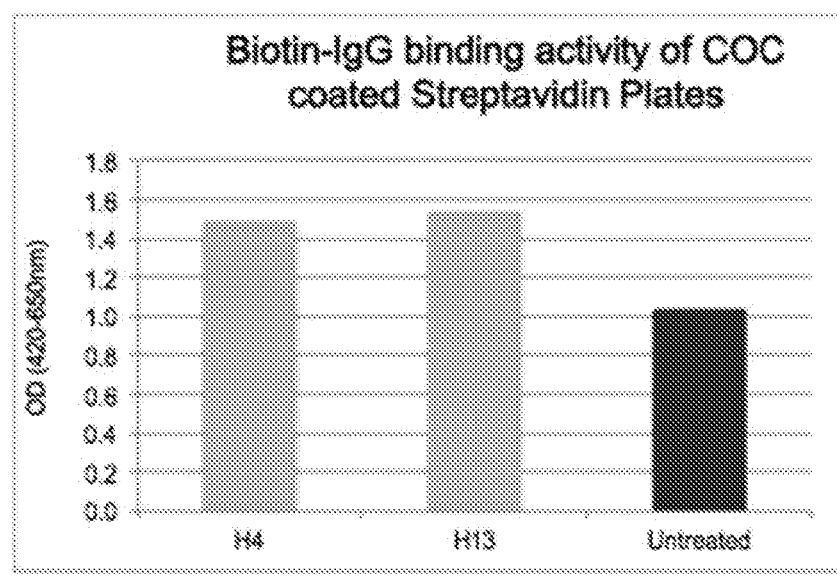
FIG. 8. Activity of streptavidin bound to COC plates, comparison of two metal-hydrophobic ligand complex-activated plates compared to untreated (passively bound) plates (H4:chromium-lauric acid 2:1; H13:chromium-lauric acid 4:1).

In this streptavidin binding study, microtitre plates produced from COC (Greiner Cat #655801) were used with 10 mM solutions of two different metal-hydrophobic ligand complexes (chromium chloride with lauric acid (2:1), referred to as "H4" in FIG. 8); Example 2A i.e. chromium with lauric acid (4:1), referred to as "H13" in FIG. 8) in water.

Streptavidin (Prozyme Cat[#] SA10) was diluted in 100 mM carbonate buffer pH 9.6 to 1.25 μg/mL. One hundred microliters was added to each well and allowed to bind for two hours at room temperature. Plates were then washed once with wash buffer (PBS and 0.1% tween 20), followed by blocking with 200 μL of 1% BSA (AusGenex Cat[#] PBSA-500 g), 2.5% sucrose in PBS for one hour at room temperature. Blocker was then aspirated from plates and plates dried overnight in a desiccant chamber.

All assays were performed with one hundred microliters of reagent loaded per well. Reagents were diluted in 1% BSA (AusGenex Cat[#] PBSA-500 g) in PBS (assay buffer). Unless otherwise stated plates were washed five times with wash buffer between each reagent addition.

Activity of bound streptavidin was determined with biotinylated mouse IgG (Jackson Immunoresearch Cat[#]015-060-003) at the following concentrations: 1, 0.5, 0.25, 0.1, 0 μg/mL in assay buffer. Biotin-mouse IgG was incubated at room temperature for thirty minutes before washing. Bound biotin-mouse-IgG was detected with goat anti-mouse HRP (Jackson Immunoresearch Cat[#]115-035-003) at 0.1 μg/mL. It was incubated at room temperature for thirty minutes at room temperature, followed by washing. Bound HRP conjugate was detected with tetramethylbenzidine (TMB Thermo scientific Cat #34021) incubated at room temperature for five minutes. The reaction was stopped with 2 M sulphuric acid. Absorbance was read at 450 nm (background reference 620 nm).

FIG. 8 shows activity of bound streptavidin determined with 0.5 μg/mL biotinylated mouse IgG (Jackson Immunoresearch Cat[#]015-060-003) and indicates that pre-treatment of COC surfaces with metal-hydrophobic ligand complexes increases the signal to noise and possibly dynamic range of streptavidin biotin-IgG binding compared to passively-coated streptavidin.

Example 13: Forming Coated QDots in Aqueous Solution

Qdots 800 ITK Organic quantum dots (Life Technologies Cat # Q21771MP) were diluted to 100 μmol/mL by adding 20 μL of stock QDot solution to 180 μL of a methanol/isopropanol (75/25%) mixture. These diluted QDots (200 μL) were added to:
a. 200 μL of 100 mM metal complex (chromic chloride with lauric acid, 2/1) in isopropanol
b. 200 μL of 100 mM metal complex (chromic chloride with lauric acid, 2/1) in d-H$_2$O
c. 200 μL of d-H$_2$O
d. 200 μL of methanol/isopropanol mixture The last control tube (e) contained only 100 mM metal complex (chromic chloride with lauric acid, 2/1) in d-H$_2$O.

All tubes were vortex for 20 seconds and incubated for 10 minutes on the bench. Then 100 μL of the sample mixture was added to a 384 well plate and a fluorescence reading was performed at excitation of 415 nm and emission of 800 nm (Tecan Infinite 200PRO Series).

Figure 9:
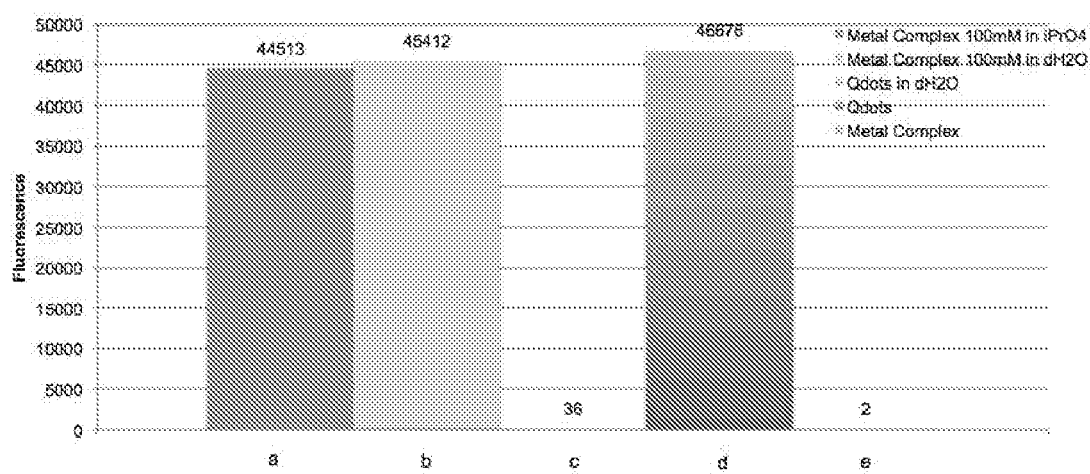
FIG. 9. Fluorescence of quantum dots (QDots) following treatment with substituted metal complex. (a) Metal complex-activated QDots in i-PrOH, (b) Metal complex-activated QDots in d-$H_2O$. (c) QDots in d-$H_2O$. (d) QDots in methanol/i-PrOH solution. (e) Substituted metal complex in d-$H_2O$.

As shown in FIG. 9, there is no fluorescence with control (e) since it does not contain QDots. There is fluorescence of QDots diluted in methanol/isopropanol solution in Control (d). Sample (b), which has metal complex in d-H$_2$O, shows equivalent fluorescence readings to control (d). However, without the metal complex (control (c)) addition of d-H$_2$O destroys colloidal stability and QDots clump/aggregate giving no fluorescence. This suggests that metal complex has coated the hydrophobic QDots to give a hydrophilic coating and allowed QDots to be well-suspended in d-H$_2$O.

The invention claimed is:

1. A modified substrate for binding of a target molecule thereon, the substrate including:
   a surface that is hydrophobic wherein the substrate is composed of a metal, a metal or metalloid composite, a synthetic polymer, a plastic, or carbon, and
   an oligomeric chromium complex layer having:
   (i) one or more chromium co-ordination sites occupied by a hydrophobic ligand for binding the oligomeric chromium complex layer to the hydrophobic surface wherein the hydrophobic ligand is of the form R—X, where X is independently selected from a carboxylic acid, aldehyde, polyalcohol, sulfonic acid, phosphonic acid, phosphate and bisulfate group, and R is independently selected from alkyl, heteroalkyl, alkenyl, alkynyl, cycloalkyl, heterocycloalkyl, alkylcycloalkyl, heteroalkylcycloalkyl, aryl, heteroaryl, aralkyl and heteroaralkyl groups which groups are optionally substituted and wherein the degree to which R—X coordinates with the oligomeric chromium complex layer is in the range of about 25% to about 75%, and
   (ii) one or more chromium co-ordination sites available for binding to a target molecule,
   wherein the hydrophobic ligand binds to the hydrophobic surface by non-covalent and non-coordinative interactions such that the co-ordination sites available for binding to a target molecule are directed away from the hydrophobic surface.

2. A modified substrate according to claim 1, wherein the modified substrate includes a target molecule bound thereto via co-ordination bonds to one or more chromium ions.

3. A modified substrate according to claim 1, wherein the substrate is substantially flat or planar.

4. A modified substrate according to claim 1, wherein the substrate is a particle.

5. A modified substrate according to claim 2, wherein the target molecule is selected from proteins, polynucleotides, carbohydrates, lipids, drugs, labelling agents, synthetic polymers and nanoparticles.

6. A modified substrate according to claim 1, wherein R—X is selected from the following acids: acetic, butyric, hexanoic, abietic, angelic, tiglic, crotonic, lauric, linoleic, linolenic, perfluorinated, gluconic, methacrylic, malonic, succinic, phthalic, acrylic, alpha and beta furyl acrylic acid, propiolic, myristic, palmitic, stearic, naphthoic, naphthenic, 6-aminohexanoic, benzoic, polyconjugated carboxylic acid polyconjugated sorbic acid, polyconjugated isocrotonic acid, polyconjugated phenylacetic acid, 3-butenoic, 7-octenoic, 9-decenoic, 11-dodecenoic, oleic, 2-cyclopentene-1-acetic, cinnamic, and behenic.

7. A modified substrate according to claim 1, further including a co-ordination ligand forming a co-ordination bond with one or more chromium ions wherein the ligand is selected from ethylenediamine, tetramethylethylenediamine, iminodiacetic acid, nitrilotriacetic acid, triphenylphosphine, oxalic acid, 1,10-phenanthroline, 8-hydroxyquinoline, salicylic acid, chloride, acetate, bromide, nitrate, perchlorate, alum, sulphate and pyridine.

8. A method of modifying a hydrophobic surface, the method including:
   providing a surface that is hydrophobic, wherein the surface is a surface of a substrate which is composed of a metal, a metal or metalloid composite, a synthetic polymer, a plastic, or carbon, and
   contacting the surface with an oligomeric chromium complex layer having:
   (i) one or more chromium co-ordination sites occupied by a hydrophobic ligand for binding the oligomeric chromium complex layer to the hydrophobic surface wherein the hydrophobic ligand is of the form R—X, where X is independently selected from a carboxylic acid, aldehyde, polyalcohol, sulfonic acid, phosphonic acid, phosphate and bisulfite group, and R is independently selected from alkyl, heteroalkyl, alkenyl, alkynyl, cycloalkyl, heterocycloalkyl, alkylcycloalkyl, heteroalkylcycloalkyl, aryl, heteroaryl, aralkyl and heteroaralkyl groups which groups are optionally substituted and wherein the degree to which R—X coordinates with the oligomeric chromium complex layer is in the range of about 25% to about 75%, and
   (ii) one or more chromium co-ordination sites available for binding to a target molecule,
   wherein the hydrophobic ligand binds to the hydrophobic surface by non-covalent and non-coordinative interactions such that the co-ordination sites available for binding to a target molecule are directed away from the hydrophobic surface, thereby forming a modified surface having increased hydrophilicity.

9. A method according to claim 8, which includes the further step of contacting the modified surface with a target molecule such that the target molecule is bound to the one or more chromium co-ordination sites available for binding to the target molecule.

10. A particle, the particle including:
    a surface that is hydrophobic, wherein the surface is a surface of a substrate which is composed of a metal, a metal or metalloid composite, a synthetic polymer, a plastic, or carbon, and
    an oligomeric chromium complex layer having:
    (i) one or more chromium co-ordination sites occupied by a hydrophobic ligand for binding the oligomeric chromium complex layer to the hydrophobic surface wherein the hydrophobic ligand is of the form R—X, where X is independently selected from a carboxylic acid, aldehyde, polyalcohol, sulfonic acid, phosphonic acid, phosphate and bisulfate group, and R is independently selected from alkyl, heteroalkyl, alkenyl, alkynyl, cycloalkyl, heterocycloalkyl, alkylcycloalkyl, heteroalkylcycloalkyl, aryl, heteroaryl, aralkyl and heteroaralkyl groups which groups are optionally substituted and wherein the degree to which R—X coordinates with the oligomeric chromium complex layer is in the range of about 25% to about 75%, and
    (ii) one or more chromium co-ordination sites available for binding to a target molecule,
    wherein the hydrophobic ligand binds to the hydrophobic surface by non-covalent and non-coordinative interactions such that the co-ordination sites available for binding to a target molecule are directed away from the hydrophobic surface.

11. A particle according to claim 10, wherein the particle is completely coated with the oligomeric chromium complex layer.

12. A particle according to claim 11, wherein the particle further includes a target molecule bound to the particle via co-ordination bonds to one or more chromium ions.

* * * * *

UNITED STATES PATENT AND TRADEMARK OFFICE
CERTIFICATE OF CORRECTION

PATENT NO. : 10,768,176 B2
APPLICATION NO. : 15/319269
DATED : September 8, 2020
INVENTOR(S) : Huang et al.

It is certified that error appears in the above-identified patent and that said Letters Patent is hereby corrected as shown below:

In the Specification

Column 10, Line 62:
Please correct "0, S" to read -- O, S --

Column 23, Line 39:
Please correct "(Antibody Binding" to read -- (Antibody Binding) --

Column 24, Line 31:
Please correct "(Streptavidin Binding" to read -- (Streptavidin Binding) --

Column 25, Line 12:
Please correct "(Antibody Binding" to read -- (Antibody Binding) --

Column 25, Line 64:
Please correct "(Streptavidin Binding" to read -- (Streptavidin Binding) --

Column 26, Line 46:
Please correct "100 μmol/mL" to read -- 100 pmol/mL --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*